US012576226B2

(12) United States Patent
Holley et al.

(10) Patent No.: US 12,576,226 B2
(45) Date of Patent: Mar. 17, 2026

(54) CHARACTERISING SYSTEMS FOR RESPIRATORY THERAPY

(71) Applicant: ResMed Pty Ltd, Bella Vista (AU)

(72) Inventors: Liam Holley, Sydney (AU);
Chinmayee Somaiya, Sydney (AU);
Dinesh Ramanan, Sydney (AU);
Gordon Joseph Malouf, Sydney (AU)

(73) Assignee: ResMed Pty Ltd (AU)

( * ) Notice: Subject to any disclaimer, the term of this patent is extended or adjusted under 35 U.S.C. 154(b) by 903 days.

(21) Appl. No.: 17/763,938

(22) PCT Filed: Oct. 13, 2020

(86) PCT No.: PCT/AU2020/051098
§ 371 (c)(1),
(2) Date: Mar. 25, 2022

(87) PCT Pub. No.: WO2021/072486
PCT Pub. Date: Apr. 22, 2021

(65) Prior Publication Data
US 2023/0053852 A1 Feb. 23, 2023

Related U.S. Application Data

(60) Provisional application No. 62/914,656, filed on Oct. 14, 2019.

(51) Int. Cl.
*A61M 16/00* (2006.01)
*A61M 16/06* (2006.01)
*A61M 16/16* (2006.01)

(52) U.S. Cl.
CPC ... *A61M 16/024* (2017.08); *A61M 2016/0027* (2013.01); *A61M 2016/0039* (2013.01);
(Continued)

(58) Field of Classification Search
CPC .............. A61M 16/00; A61M 16/0066; A61M 16/0069; A61M 16/024; A61M 16/06;
(Continued)

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| AU | 2013206410 B2 | 4/2016 |
| CN | 107961428 A | 4/2018 |

(Continued)

OTHER PUBLICATIONS

Extended European Search Report from corresponding EP Application No. 20876574.3 dated Oct. 12, 2023 (6 pp.).
(Continued)

*Primary Examiner* — Joseph D. Boecker
(74) *Attorney, Agent, or Firm* — Botos Churchill IP Law LLP

(57) ABSTRACT

Apparatus and methods provide system characterisation such as for operation of respiratory treatment apparatus. Such a characterisation may include a determination of a patient interface type and/or an event such as a leak or blocked vent. For a characterisation, one or more controller(s) or processor(s) may be configured to make a determination of parameters that best fit a template curve, such as a quadratic function, to a plurality of measurements, such as data points. Each data point may include a pressure value, and a flow rate value at the pressure value. Parameters from the function may then be applied, such as with a data structure to characterize the system, such as with an identification of the patient interface type from the parameters. In some versions, parameter(s) of operation of the apparatus
(Continued)

11000

Apply low-pass filter to total flow rate and device pressure — 11010

For each value of filtered device pressure, find the bias flow rate from the histogram of values of filtered total flow rate at that filtered device pressure — 11020

Fit a pressure-flow curve to the points (bias flow rate, filtered device pressure) — 11030

Identify patient interface from pressure-flow curve parameters — 11040 may be adjusted based on the characterisation, such as by using the parameters of the template.

52 Claims, 21 Drawing Sheets

(52) U.S. Cl.
CPC ......... *A61M 16/0069* (2014.02); *A61M 16/06* (2013.01); *A61M 16/16* (2013.01); *A61M 2205/15* (2013.01); *A61M 2205/3334* (2013.01); *A61M 2205/3344* (2013.01)

(58) Field of Classification Search
CPC .. A61M 2016/0027; A61M 2016/0039; A61M 2205/3334; A61M 2205/3344; A61B 5/0826; A61B 5/4818
See application file for complete search history.

(56)                References Cited

U.S. PATENT DOCUMENTS

| | | | |
|---|---|---|---|
| 7,866,944 | B2 | 1/2011 | Kenyon et al. |
| 8,636,479 | B2 | 1/2014 | Kenyon et al. |
| 8,638,014 | B2 | 1/2014 | David |
| 2004/0074495 | A1* | 4/2004 | Wickham .......... A61M 16/0858 128/204.23 |
| 2007/0144519 | A1* | 6/2007 | Henry ................... A61M 16/00 128/204.21 |
| 2008/0251075 | A1* | 10/2008 | Scarberry ......... A61M 16/0051 600/529 |
| 2010/0258123 | A1* | 10/2010 | Somaiya ........... A61M 16/0069 128/204.23 |
| 2011/0313689 | A1* | 12/2011 | Holley .............. A61M 16/0069 702/56 |
| 2012/0247470 | A1* | 10/2012 | Ho .................... A61M 16/0066 128/204.21 |
| 2017/0266400 | A1* | 9/2017 | McCarthy ............. A61M 16/06 |

FOREIGN PATENT DOCUMENTS

| | | |
|---|---|---|
| CN | 108290018 A | 7/2018 |
| EP | 1800705 A2 | 6/2007 |
| EP | 2106818 A1 | 10/2009 |
| WO | 2011077274 A1 | 6/2011 |
| WO | 2013020167 A1 | 2/2013 |
| WO | 2019006496 A1 | 1/2019 |

OTHER PUBLICATIONS

Examination Report No. 1 in AU Application No. 2020367830 dated Feb. 10, 2025. 2 pages.
Office Action issued in corresponding Chinese Patent Application No. 2020800866807, mailed Jun. 30, 2025, 18 pages.
International Preliminary Report on Patentability for International Application No. PCT/AU2020/051098, Date of Mailing: Aug. 30, 2021.
The International Search Report of the International Searching Authority for International Application No. PCT/AU2020/051098, Date of Mailing: Jan. 20, 2021.
The Written Opinion of International Application No. PCT/AU2020/051098, Date of Mailing: Jan. 20, 2021.
West, John B., "Respiratory Physiology", Lippincott Williams & Wilkins, 9th Edition published 2012.
Notice of Acceptance issued in corresponding Australian Patent Application No. 2020367830, mailed Oct. 15, 2025, 3 pages.

* cited by examiner

Nasal cavity

Oral cavity

Larynx

Vocal folds

Oesophagus

Trachea

Alveolar sacs

Bronchus

Lung

Heart

Diaphragm

Copyright 2012 ResMed Limited

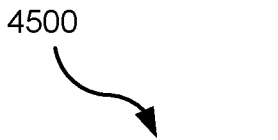
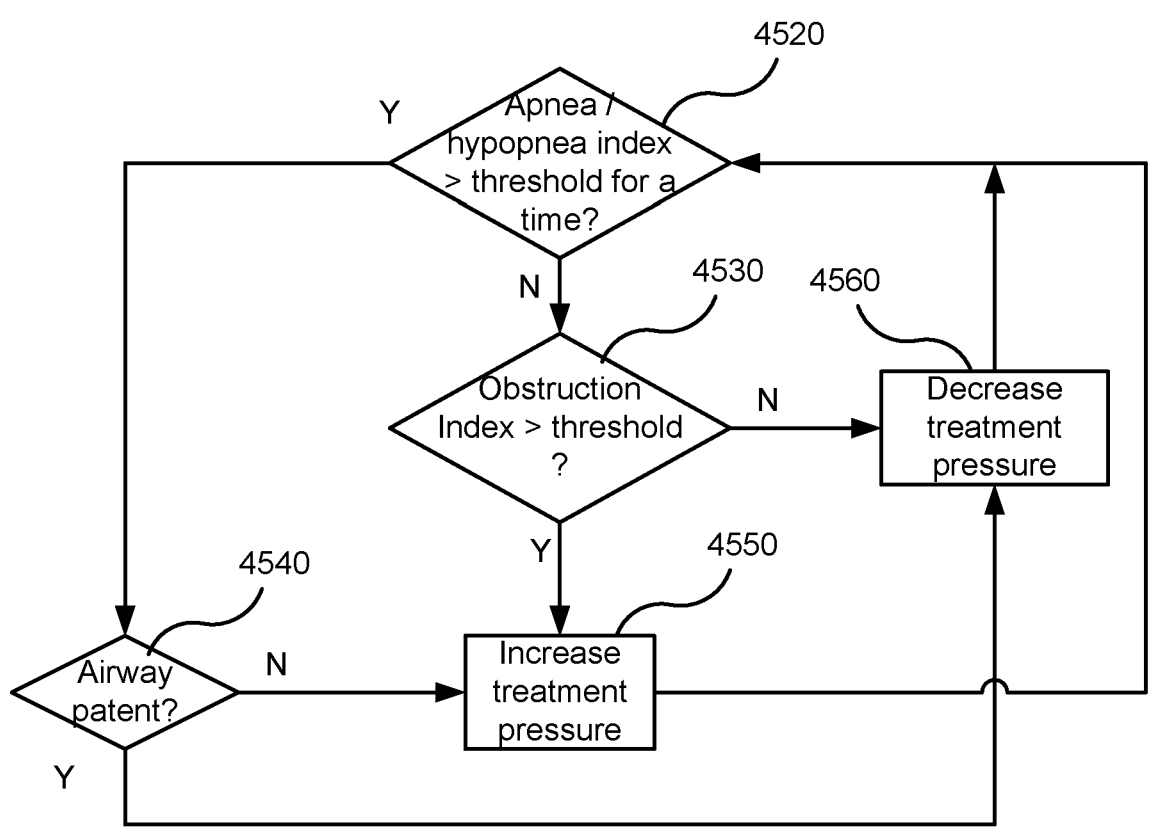
FIG. 4E

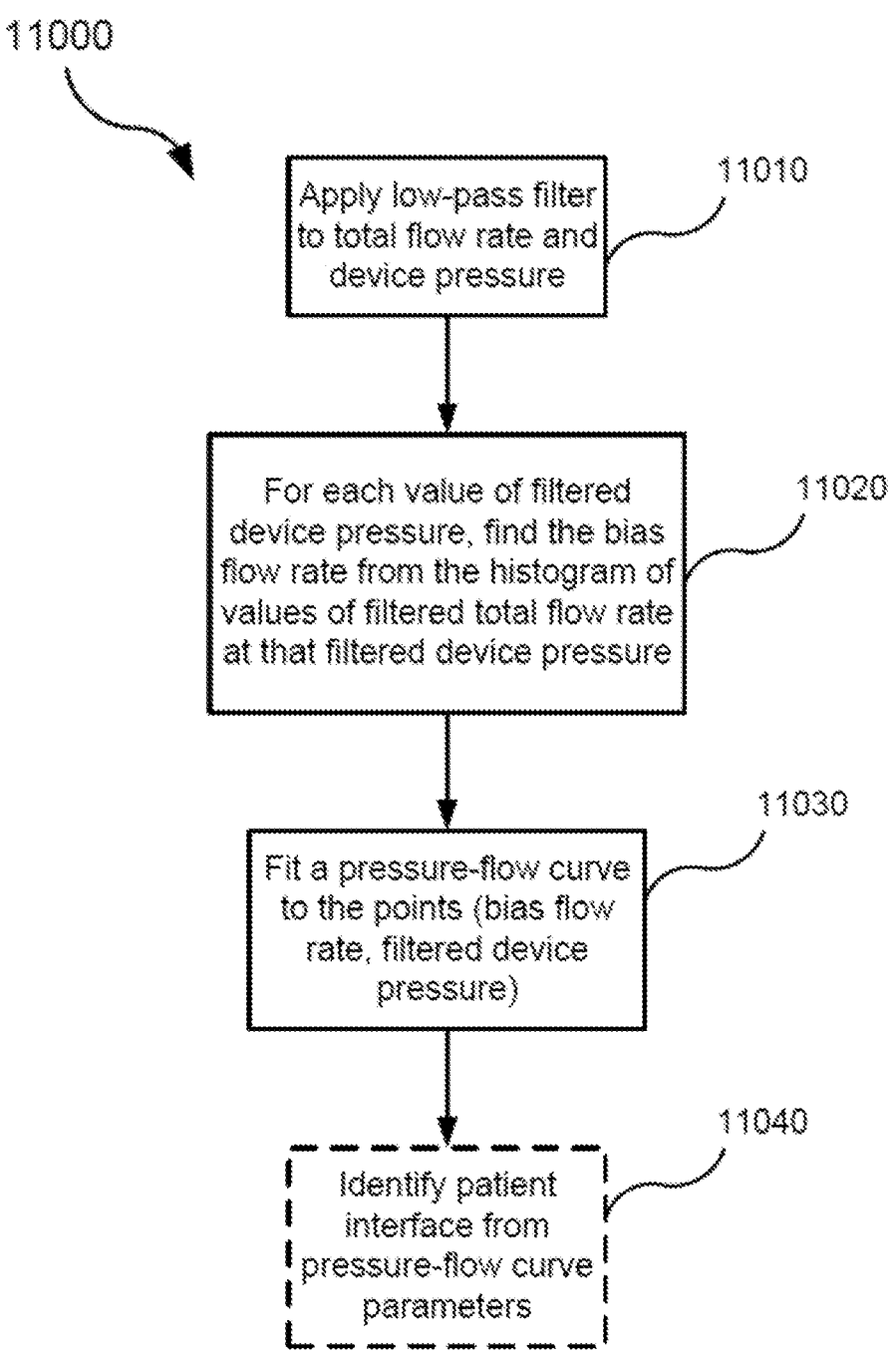

11000

11010
Apply low-pass filter to total flow rate and device pressure

11020
For each value of filtered device pressure, find the bias flow rate from the histogram of values of filtered total flow rate at that filtered device pressure 11030
Fit a pressure-flow curve to the points (bias flow rate, filtered device pressure)

11040
Identify patient interface from pressure-flow curve parameters

FIG. 11

CHARACTERISING SYSTEMS FOR RESPIRATORY THERAPY

1. CROSS-REFERENCE TO RELATED APPLICATIONS

The present application is a national phase entry under 35 U.S.C. § 371 of International Application No. PCT/AU2020/051098, filed Oct. 13, 2020, published in English, which claims priority from U.S. Provisional Application No. 62/914,656, filed Oct. 14, 2019, all of which are incorporated herein by reference.

This application claims the benefit of U.S. Provisional Application No. 62/914,656, filed 14 Oct. 2019, the entire disclosure of which is hereby incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV) and Invasive ventilation (IV) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's respiratory cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus, RPT devices may also be configured to act as flow therapy devices. Examples of RPT devices include a CPAP device and a ventilator.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air. Humidifiers therefore often have the capacity to heat the flow of air was well as humidifying it.

2.2.4 Component Identification

As previously mentioned, a respiratory therapy system typically includes components such as an RPT device, a humidifier, an air circuit, and a patient interface. A variety of different forms of patient interface may be used with a given RPT device, for example a nasal pillows, nasal prongs, nasal mask, nose and mouth (oronasal) mask, or full face mask. Furthermore, different lengths and diameters of air circuit may be used. In order to provide improved control of therapy delivered to the patient interface, it may be advantageous to estimate treatment parameters such as pressure in the patient interface, leak flow rate, and vent flow rate. In systems using estimation of treatment parameters, knowledge of the type of component being used by a patient can enhance the accuracy of treatment parameter estimation, and therefore the efficacy of therapy.

To obtain knowledge of component type, some RPT devices include a menu system that allows the patient to enter or select the type of system components, including the patient interface, being used, e.g., brand, form, model, etc. Once the types of the components are entered by the patient, the RPT device can select appropriate operating parameters of the flow generator that best coordinate with the selected components, and can more accurately monitor treatment parameters during therapy. However, patients may not select the type of component correctly, or at all, leaving the RPT device in error or ignorant about the type of component in use.

In the past, an array of solutions has been employed, or proposed, in the field of respiratory therapy in relation to component identification. However, integrating costly electrical and/or mechanical features to the frequently replaced component(s), such as the patient interface, may be detrimental to providing a cost-effective therapy, and potentially environmentally unsustainable due to the increased waste.

Furthermore, many proposed solutions in relation to sensors and/or transducers may be limited in that if a sensor is proposed to be located remotely from where its data is to be saved and/or analysed, often this may further increase a complexity and/or cost of implementation. For example, where a patient interface comprises a sensor, it may require an electrical connection to the RPT device, which may further increase a complexity and/or cost of implementation.

Also, designers of RPT devices face numerous choices, and often arrive at different solutions when compared to other devices on the market such as by a competitor, or indeed, by the same manufacturer but produced at a different time. As a result, the associated electrical connector provided may be only connectible to a particular RPT device. This may have an unintended effect of creating incompatibility which can be a disadvantage to a particular sub-segment of consumers, and/or it may reduce consumer choice.

There is therefore a need for improved apparatus and methods for characterisation of, such as automatic identification of components in, respiratory therapy systems, and more accurate estimation of therapy parameters such as leak flow rates.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

The disclosed technology concerns apparatus and methods for automated characterisation of a respiratory therapy system, such as by statistical analysis of sensor signals over a period of therapy, in a manner that is robust to leak. In addition, the apparatus and methods may be configured to estimate the leak flow rate during a period of therapy based on the characterisation of the therapy system. A property of the respiratory therapy may be adjusted based on the characterisation and/or the estimated leak flow rate.

Some implementations of the present technology may include apparatus for respiratory therapy. The apparatus may include a pressure generator configured to generate a flow of air to a patient interface for a respiratory therapy for a patient. The apparatus may include a pressure transducer configured to generate a signal representing a pressure of the flow of air. The apparatus may include a flow rate transducer configured to generate a signal representing a flow rate of the flow of air. The apparatus may include a controller. The controller may be configured to receive the pressure signal and the flow rate signal from the transducers. The controller may be configured to analyse the pressure signal and the flow rate signal to identify the patient interface. The apparatus may include a central controller of the pressure generator. The central controller may be configured to receive the identification of the patient interface. The central controller may be configured to control the pressure generator to adjust a property of the flow of air based on the identification. The analysis may include a determination of parameters that best fit a template curve to a plurality of points. Each of the plurality of points may include: (a) a pressure value, and (b) a flow rate value at the pressure value.

In some implementations, the controller may be the central controller of the pressure generator. The controller may be a processor of a remote external device in communication with the central controller of the pressure generator. The central controller may be configured to determine an identification of the patient interface based on the determination of parameters. The central controller may be configured to determine a control parameter for adjustment of a property of the flow of air. The central controller may be configured to adjust the control parameter based on the determination of the parameters. The pressure value may be a value of a low-pass filtered version of measured pressure from the pressure signal. The flow rate value may be a mode of a histogram of values of measured flow rate from the flow rate signal at the pressure value. The controller may be configured to determine the mode of the histogram of values, and wherein the histogram of values may be a histogram of a low-pass filtered version of measured flow rate from the flow rate signal at the pressure value. The controller may be configured to subtract a pressure drop from a measured pressure value from the pressure signal for the analysing. The pressure drop may be a pressure drop of an air circuit connecting the apparatus to the patient interface at a measured flow rate from the flow rate signal.

In some implementations, the controller may be configured to determine the plurality of points during a therapy session may include automatic positive airway pressure (APAP) therapy. The controller may be configured to condition the analysis on checking of a time of therapy use and/or a range of provided therapy pressures of a therapy session. The controller may be configured to estimate a leak flow rate from measured pressure from the pressure signal, measured flow rate from the flow rate signal, and the determined parameters. The controller may be configured to determine a bias flow rate based on a pressure-flow curve defined by the determined parameters. The controller may be configured to determine the leak flow estimate by subtracting the bias flow rate from the measured flow rate, wherein the measured flow rate may be a total flow rate. The pressure-flow curve defined by the determined parameters may include a quadratic function. The controller may be configured to determine the bias flow rate by inverting the pressure-flow curve defined by the determined parameters. The controller may be configured to estimate a respiratory flow rate of the patient from the measured flow rate, the measured pressure, the determined parameters, and the estimated leak flow rate. To control the adjustment to the property of the flow of air, the central controller may be configured to detect an event from the estimated respiratory flow rate of the patient, and may be configured to adjust a treatment pressure of the flow of air in response to the detected event. The event may be an event from the group consisting of: an apnea, a hypopnea, a snore, and inspiratory flow limitation.

In some implementations, the analysis of the apparatus may further include a comparison of the determined parameters with a plurality of sets of parameters in a database. The analysis of the apparatus may further include an identification of the patient interface based on the comparison of the determined parameters. The template curve may be a quadratic function. The controller may be configured to determine a vent blocking event based on the determined parameters. The controller may be configured to determine the vent blocking event based on comparing a measure of average total flow rate with a flow rate at a given device pressure according to a function comprising the determined parameters. The controller may be configured to generate an indication of the vent blocking event such as if the measure of average total flow rate is less than the flow rate according to the function.

Some implementations of the present technology may include a method of operating in a respiratory treatment apparatus that may be configured to generate a flow of air to a patient interface for a respiratory therapy for a patient. The method may include accessing data representing a measured pressure of the flow of air, the measured pressure generated using a pressure transducer. The method may include accessing data representing a measured flow rate of the flow of air, the measured flow rate generated using a flow rate transducer. The method may include analysing, in a controller, the measured pressure and the measured flow rate to identify the patient interface. The analysing may include determining parameters that best fit a template curve to a plurality of points. Each point of the plurality of points may include: (a) a pressure value, and (b) a flow rate value at the pressure value.

In some implementations, the controller may determine an identification of the patient interface based on the determining of parameters. The method may further include controlling, in the controller, a determination of a value of a control parameter for operating a pressure generator of the respiratory treatment apparatus based on the identification of the patient interface. The method may further include deriving the pressure value by low-pass filtering the measured pressure. The method may further include determining the flow rate value by deriving a histogram of values of the measured flow rate at the pressure value and determining a mode of the histogram. Deriving the histogram may include determining values of a low-pass filtered version of the measured flow rate at the pressure value. The method may further include subtracting a pressure drop value from the measured pressure for the analysing. The pressure drop value may represent a pressure drop of an air circuit connecting the respiratory treatment apparatus to the patient interface at the measured flow rate. The controller may determine values for the plurality of points with data from a therapy session that may include automatic positive airway pressure (APAP) therapy. The method may further include conditioning the analysis on checking of a time of therapy use and/or a range of provided therapy pressures of a therapy session. The method may further include estimating a leak flow rate from the measured pressure, the measured flow rate, and the determined parameters. The method may further include determining a bias flow rate based on a pressure-flow curve defined by the determined parameters. Determining the leak flow estimate may include subtracting the bias flow rate from the measured flow rate. The measured flow rate may be a total flow rate.

In some implementations, the pressure-flow curve defined by the determined parameters may include a quadratic function. The method may further include determining the bias flow rate by inverting the pressure-flow curve defined by the determined parameters. The method may further include estimating a respiratory flow rate of a patient from the measured flow rate, the measured pressure, the determined parameters, and the estimated leak flow rate. The method may further include detecting an event from the estimated respiratory flow rate of the patient. The method may further include adjusting a treatment pressure of the flow of air in response to the detected event. The event may be an event from the group consisting of: an apnea, a hypopnea, a snore, and inspiratory flow limitation. The analysing may further include comparing the determined parameters to a plurality of sets of parameters in a database. The analysing may further include identifying the patient interface based on the determined parameters. The template curve may be a quadratic function. The method may further include determining a vent blocking event based on the determined parameters. The determining of the vent blocking event may include comparing a measure of average total flow rate with a flow rate at a given device pressure according to a function comprising the determined parameters. The method may include generating an indication of the vent blocking event such as if the measure of average total flow rate is less than the flow rate according to the function.

Some implementations of the present technology may include. a processor readable medium configured with program instructions for controlling one or more processors to execute a method of operating a respiratory treatment apparatus. The method may include any one or more of the steps of the operations of the method(s) described herein.

Some implementations of the present technology may include. respiratory treatment apparatus. The respiratory treatment apparatus may include a pressure generator configured to generate a flow of air to a patient interface for a respiratory therapy for a patient. The respiratory treatment apparatus may include a pressure transducer configured to generate a signal representing a pressure of the flow of air. The respiratory treatment apparatus may include a flow rate transducer configured to generate a signal representing a flow rate of the flow of air. The respiratory treatment apparatus may include a controller. The controller may include one or more processors with any of the processor readable mediums described herein.

Some implementations of the present technology may include a system for controlling a respiratory therapy. The system may include means for supplying a flow of air to a patient interface as a respiratory therapy. The system may include means for generating a flow rate signal representing a flow rate of the flow of air. The system may include means for generating a pressure signal representing a pressure of the flow of air. The system may include means for analysing the flow rate signal and the pressure signal to identify the patient interface. The system may include means for adjusting a property of the flow of air based on the identified patient interface. The analysing of the means for analyzing may include determining of parameters that best fit a template curve to a plurality of points, each point may include: (a) a pressure value, and (b) a flow rate value at the pressure value.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown.

4.2 Respiratory System and Facial Anatomy

Figure 1A:
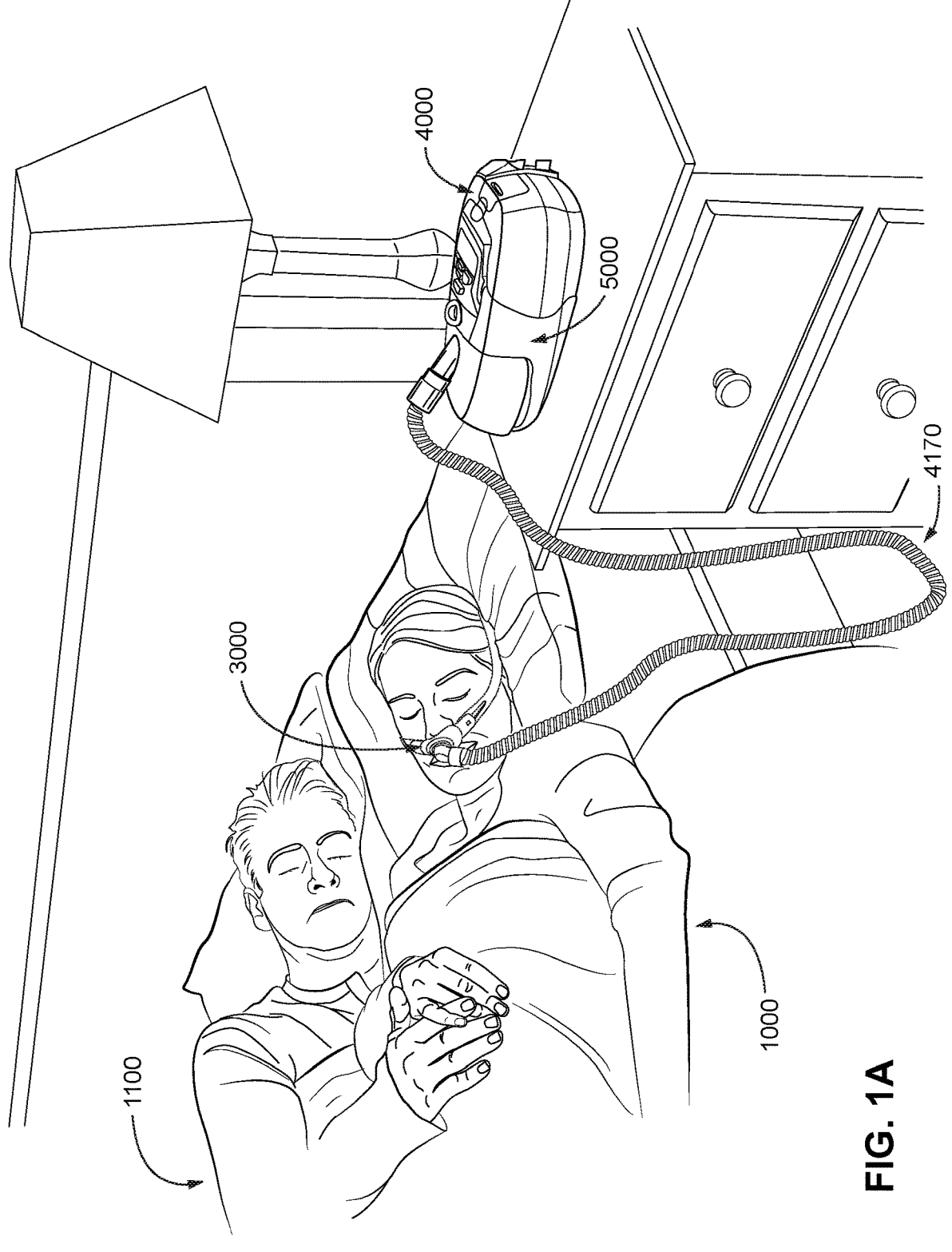
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
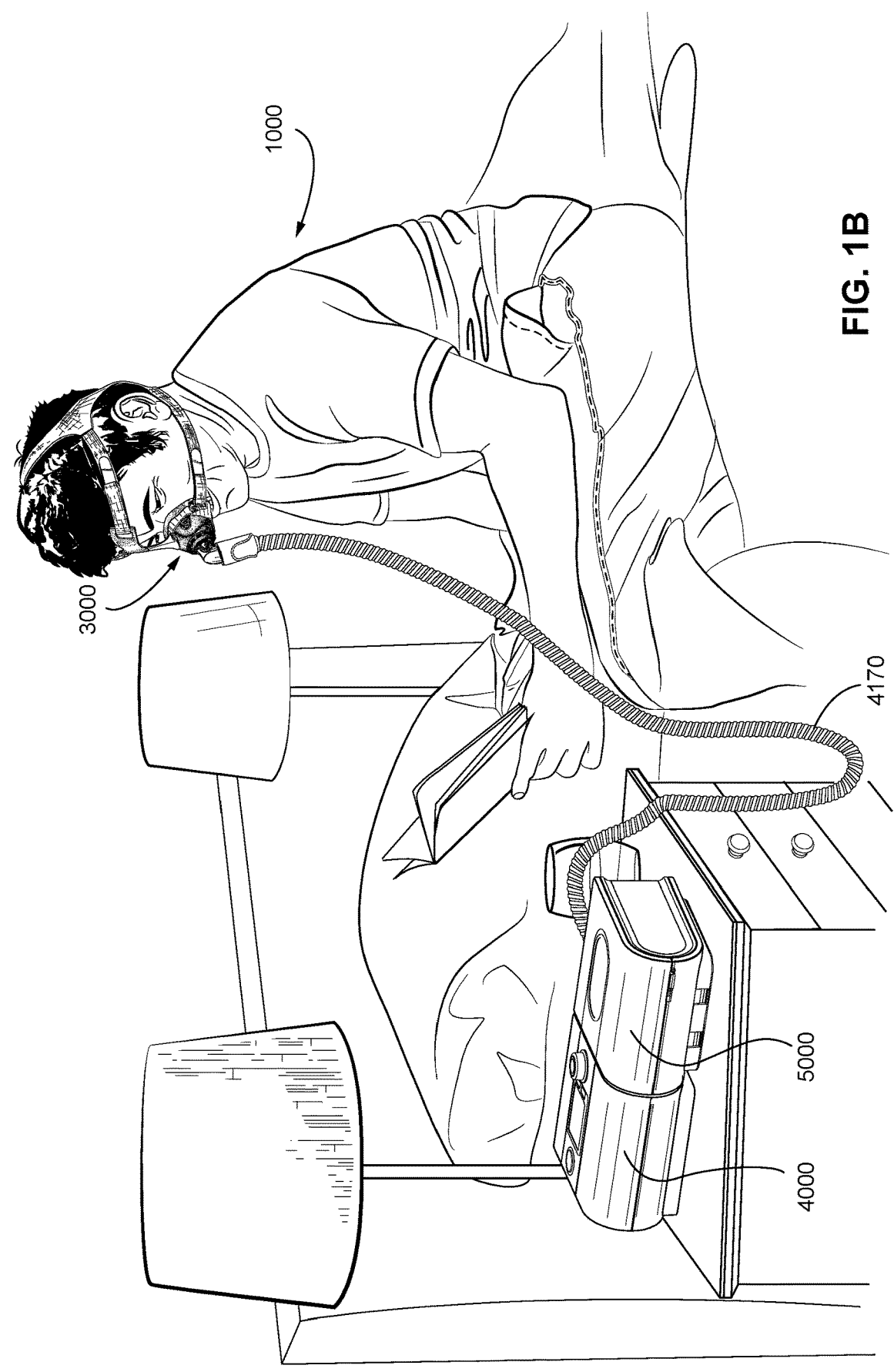
Figure 1C:
Figure 2:
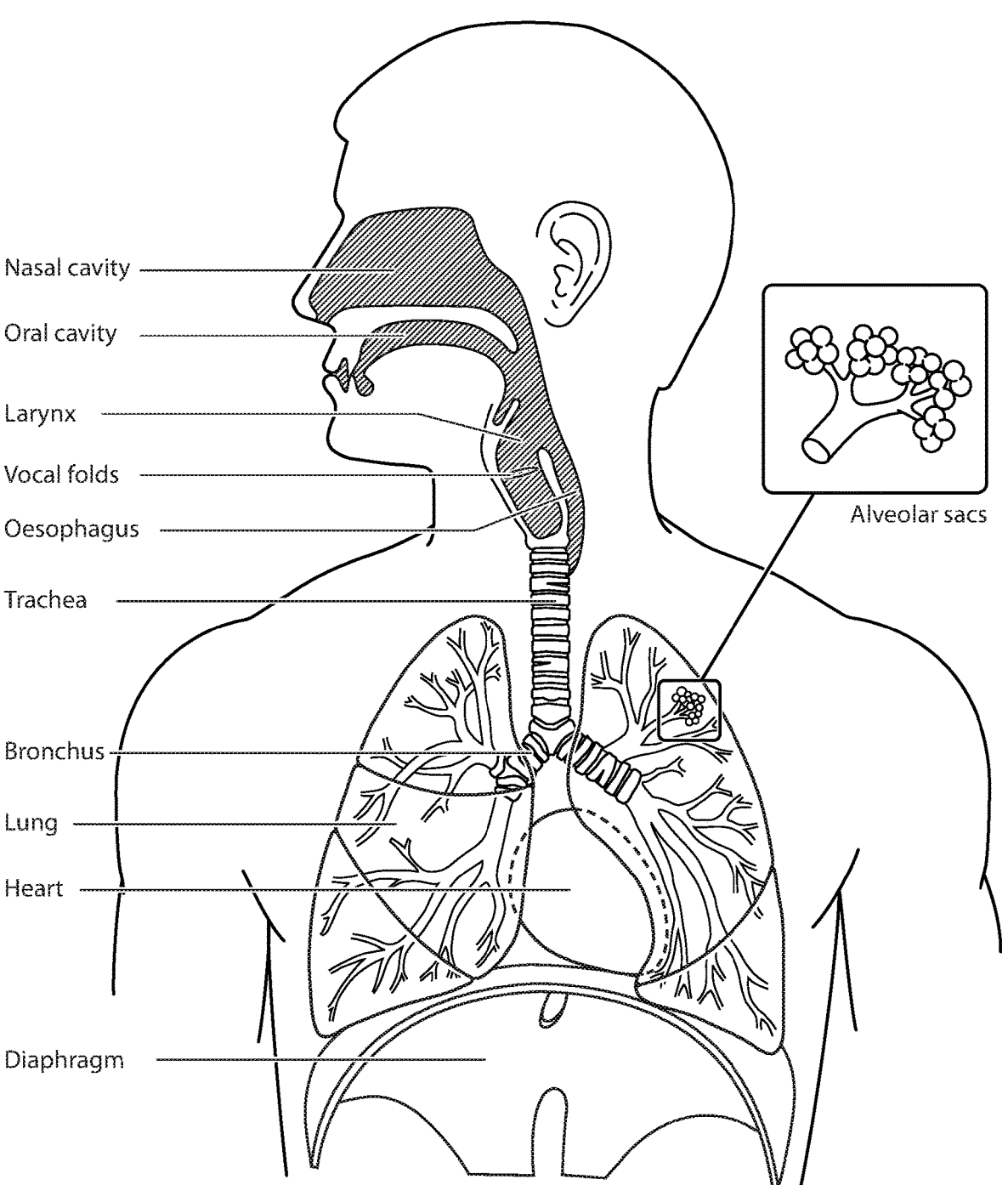

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

Figure 3:
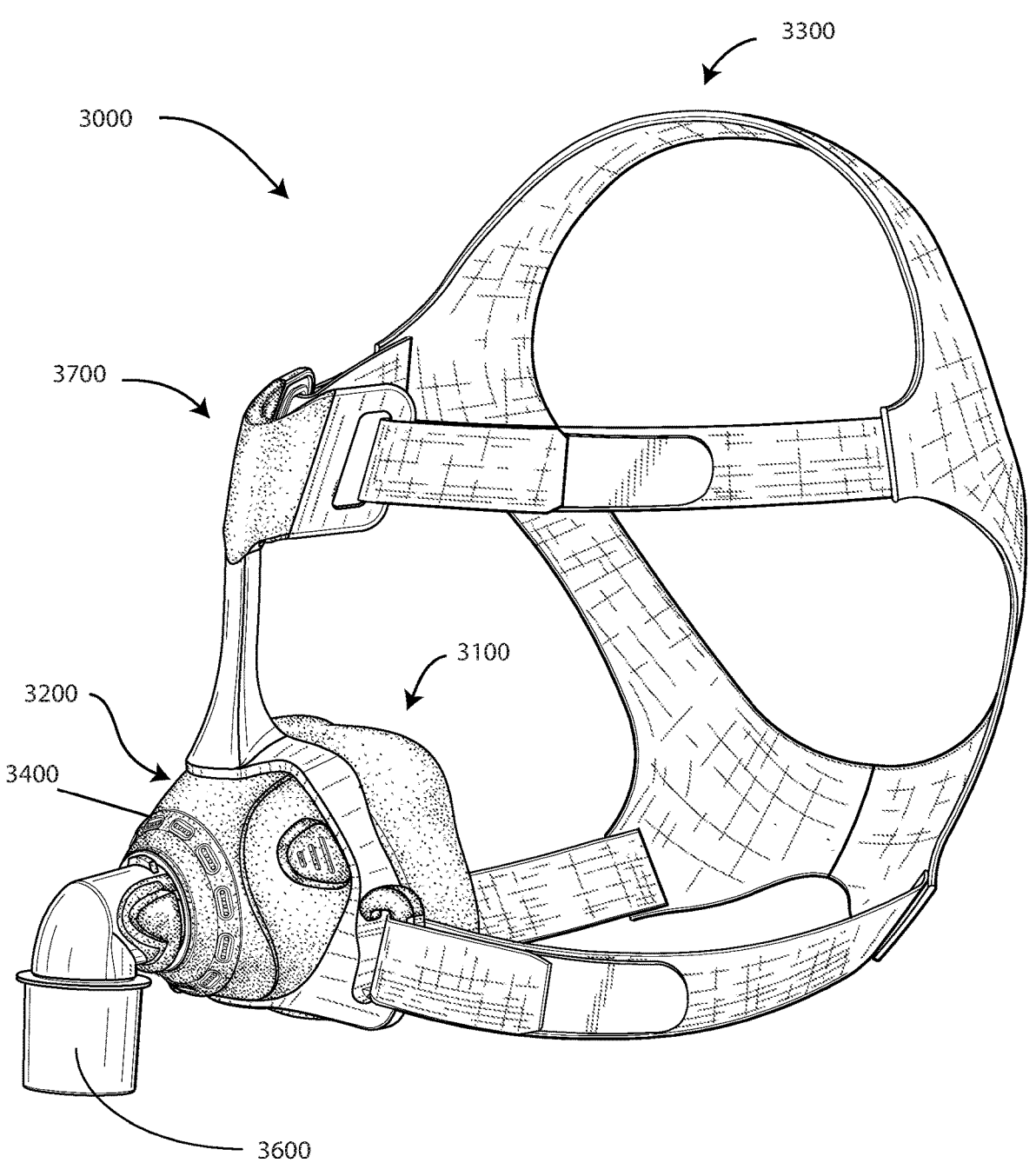

FIG. 3 shows a patient interface in the form of a nasal mask in accordance with one form of the present technology.

4.4 RPT Device

Figure 4A:
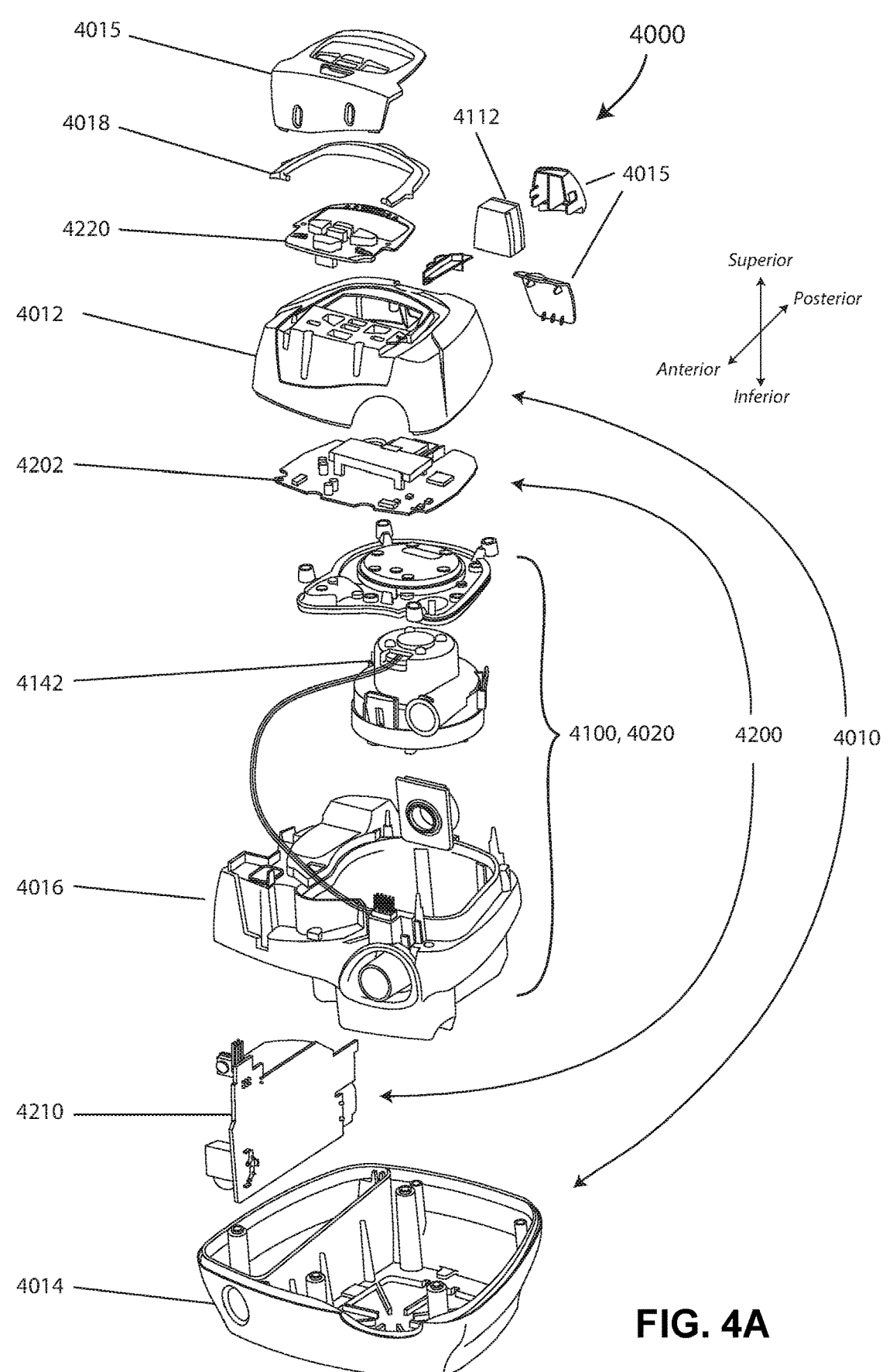

FIG. 4A shows an RPT device in accordance with one form of the present technology.

Figure 4B:
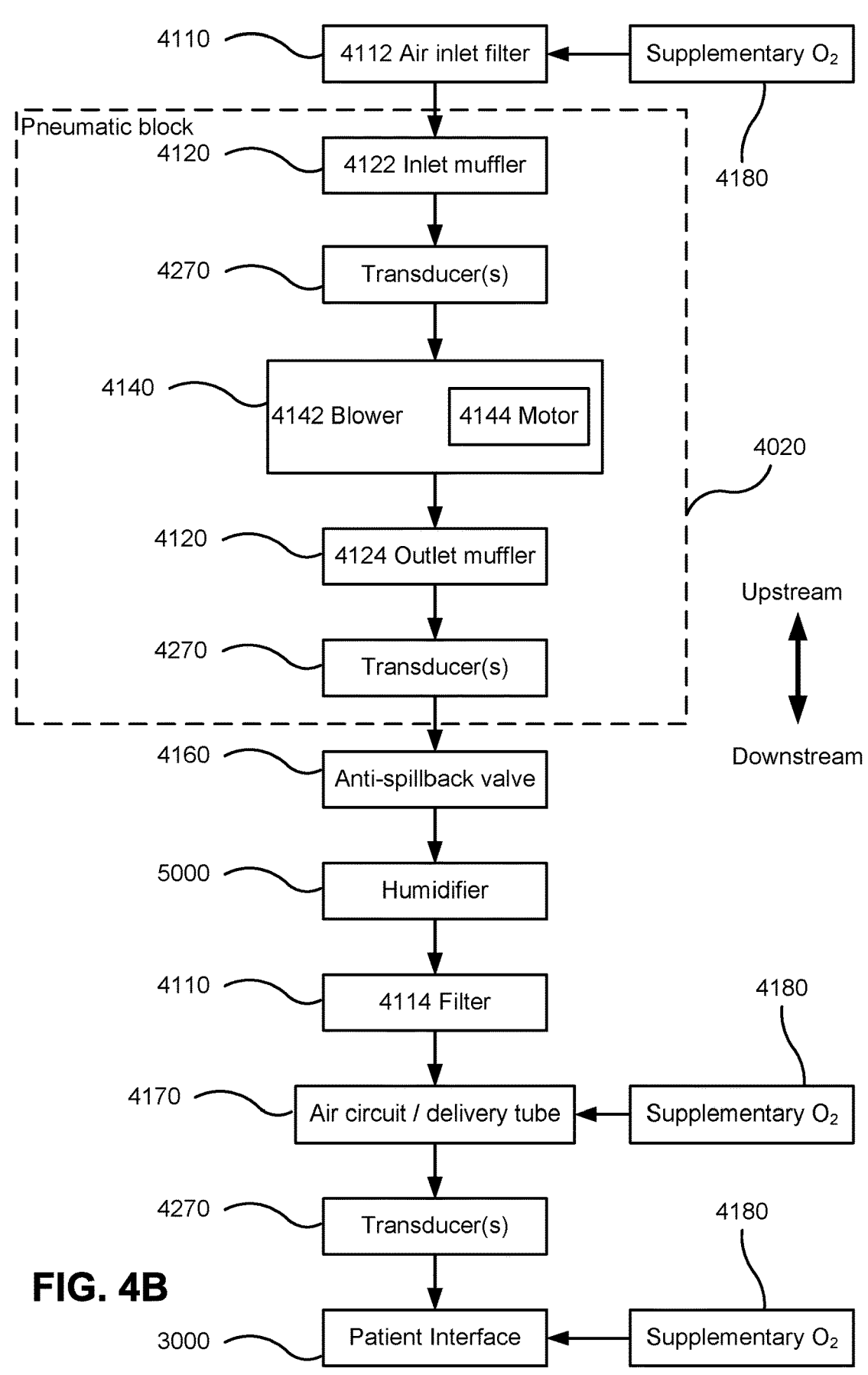

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
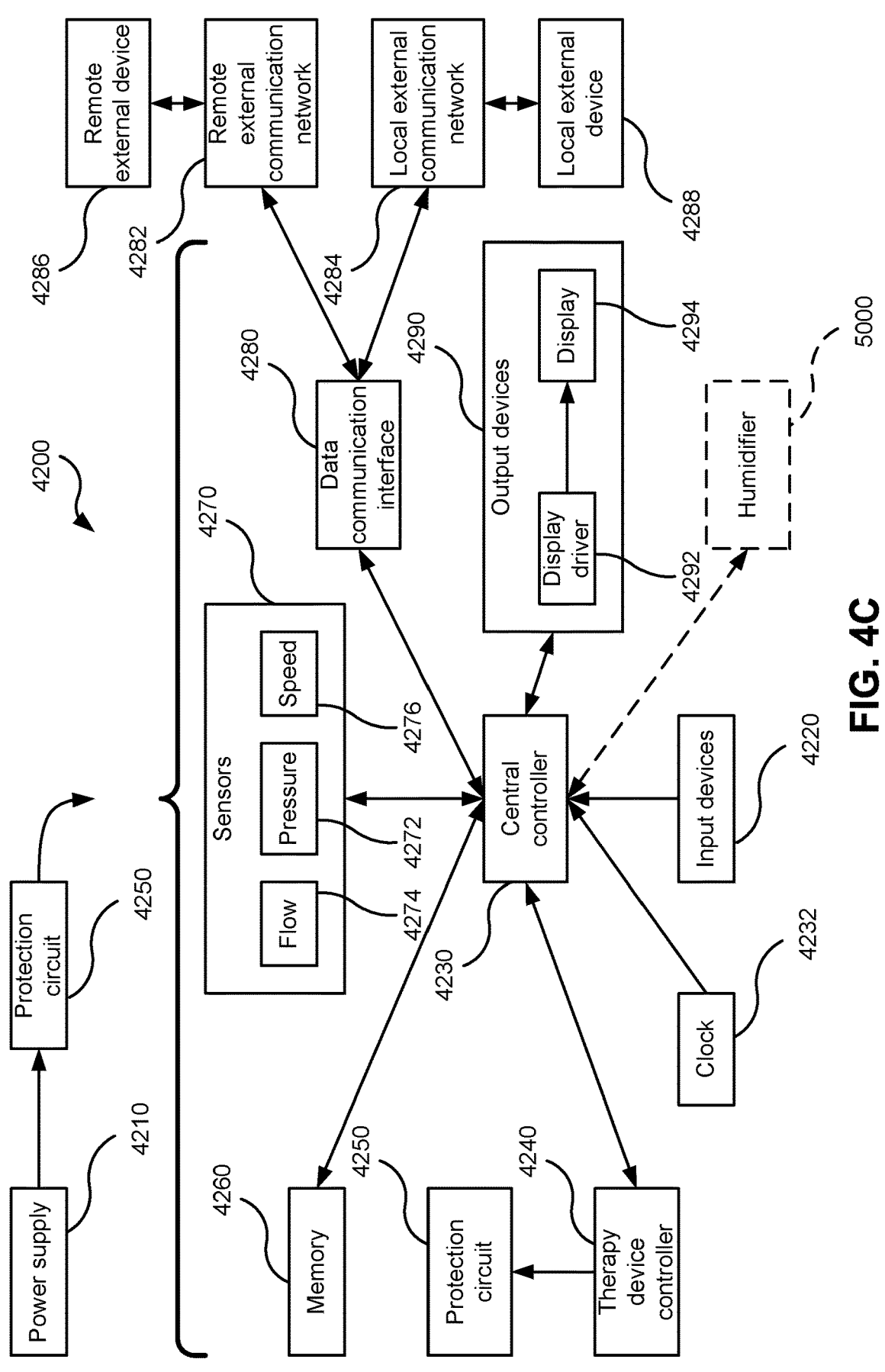

FIG. 4C is a schematic diagram of the electrical components of an RPT device in accordance with one form of the present technology.

Figure 4D:
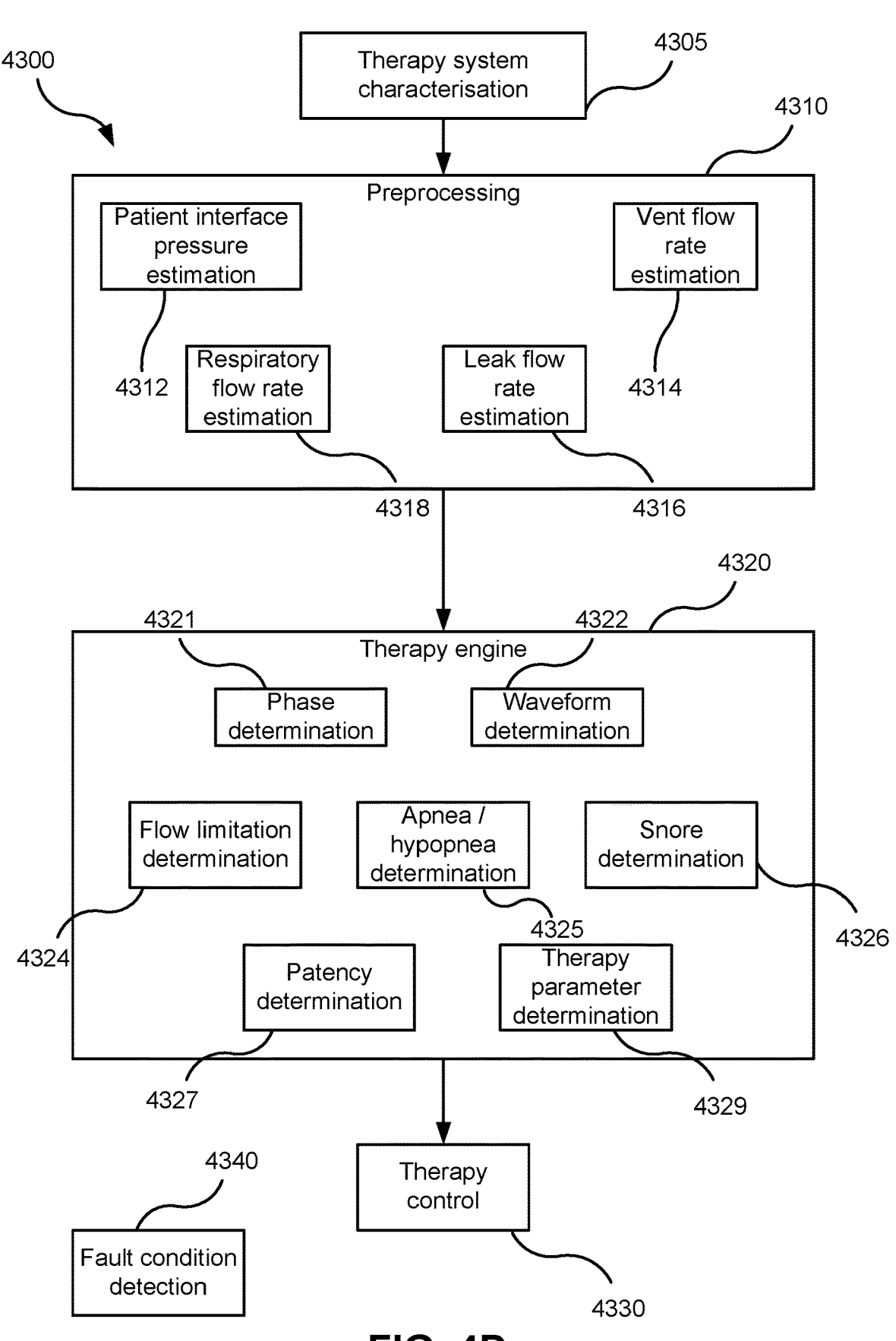

FIG. 4D is a schematic diagram of the algorithms implemented in an RPT device in accordance with one form of the present technology.

FIG. 4E is a flow chart illustrating a method carried out by the therapy engine module of FIG. 4D in accordance with one form of the present technology.

4.5 Humidifier

Figure 5A:
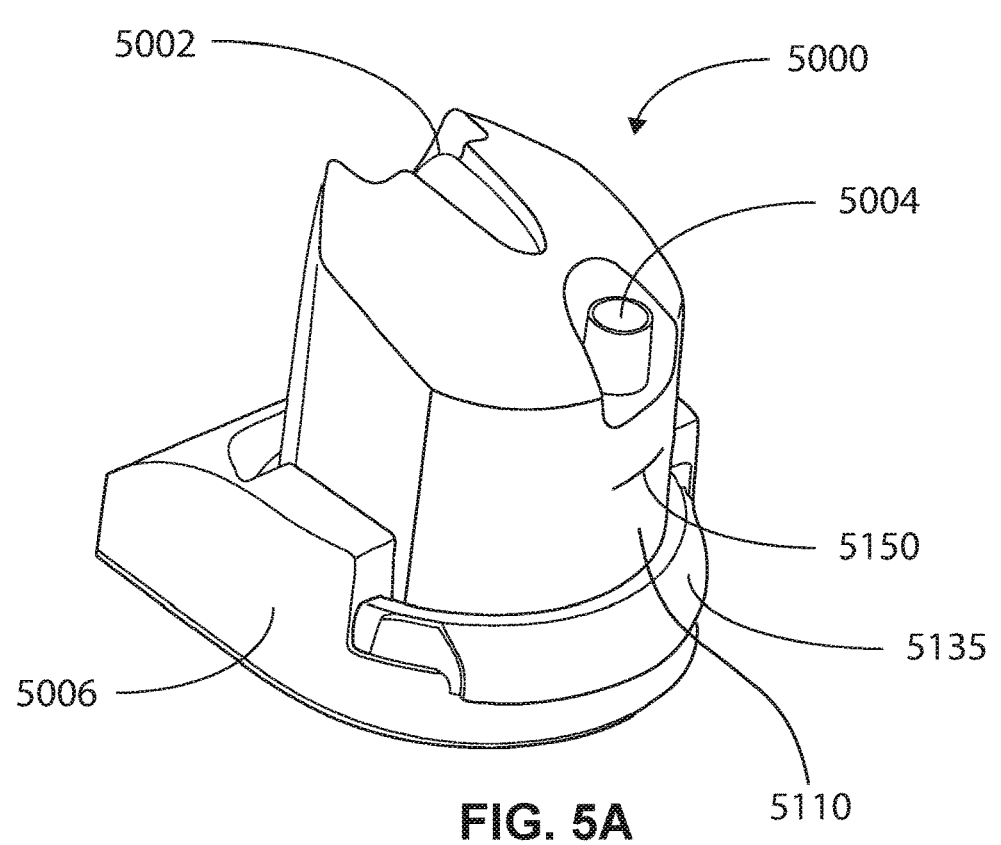

FIG. 5A shows an isometric view of a humidifier in accordance with one form of the present technology.

Figure 5B:
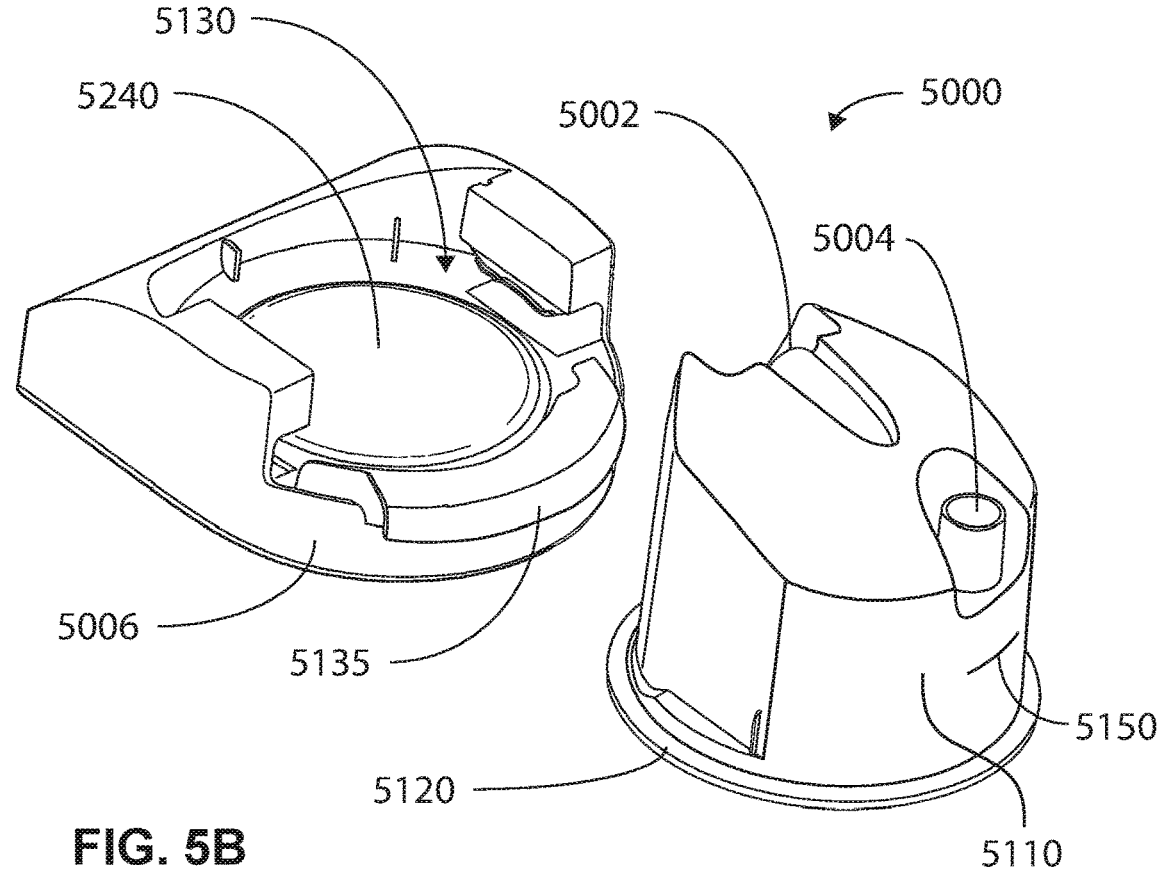

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
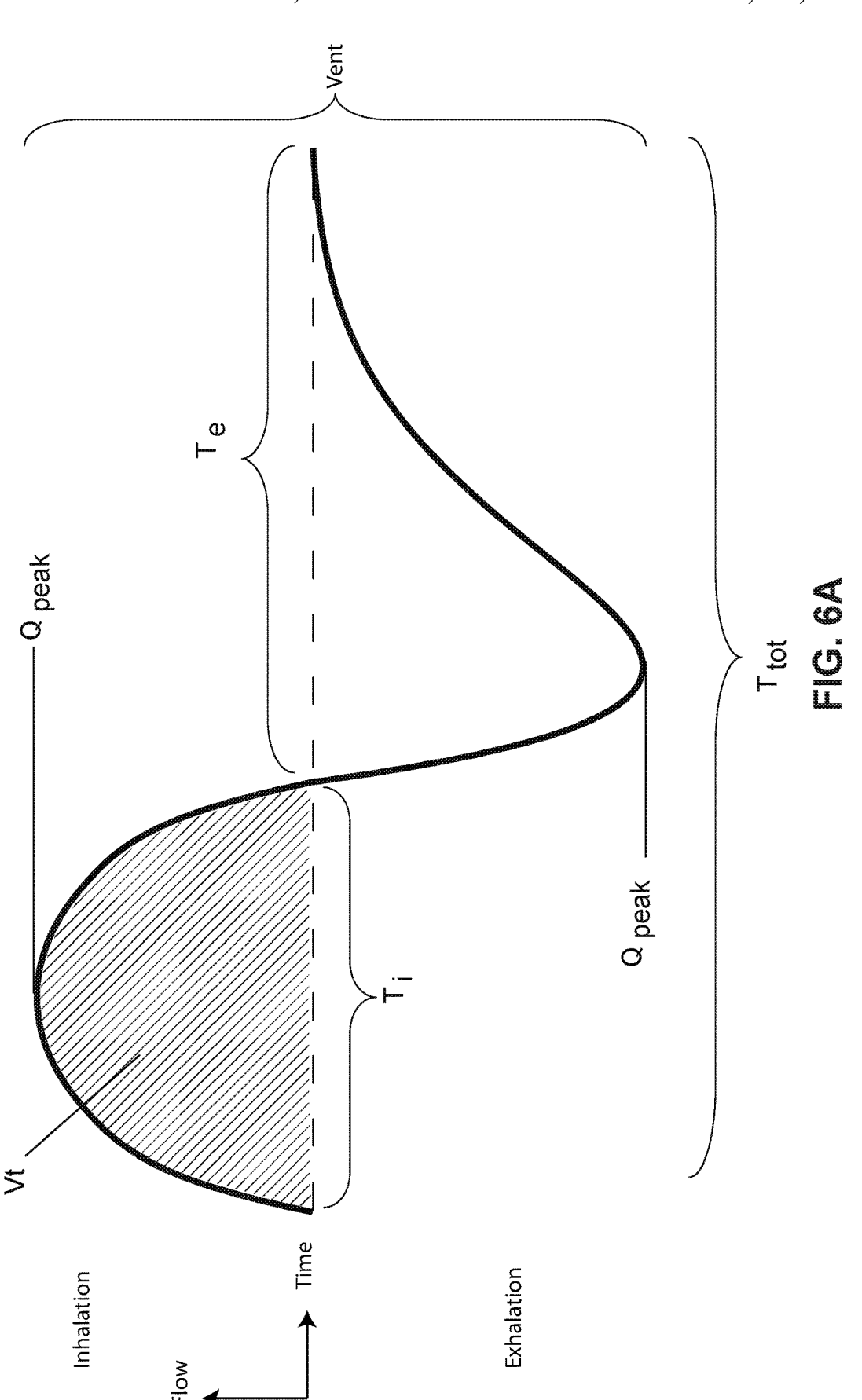

FIG. 6A shows a model typical breath waveform of a person while sleeping.

Figure 6B:
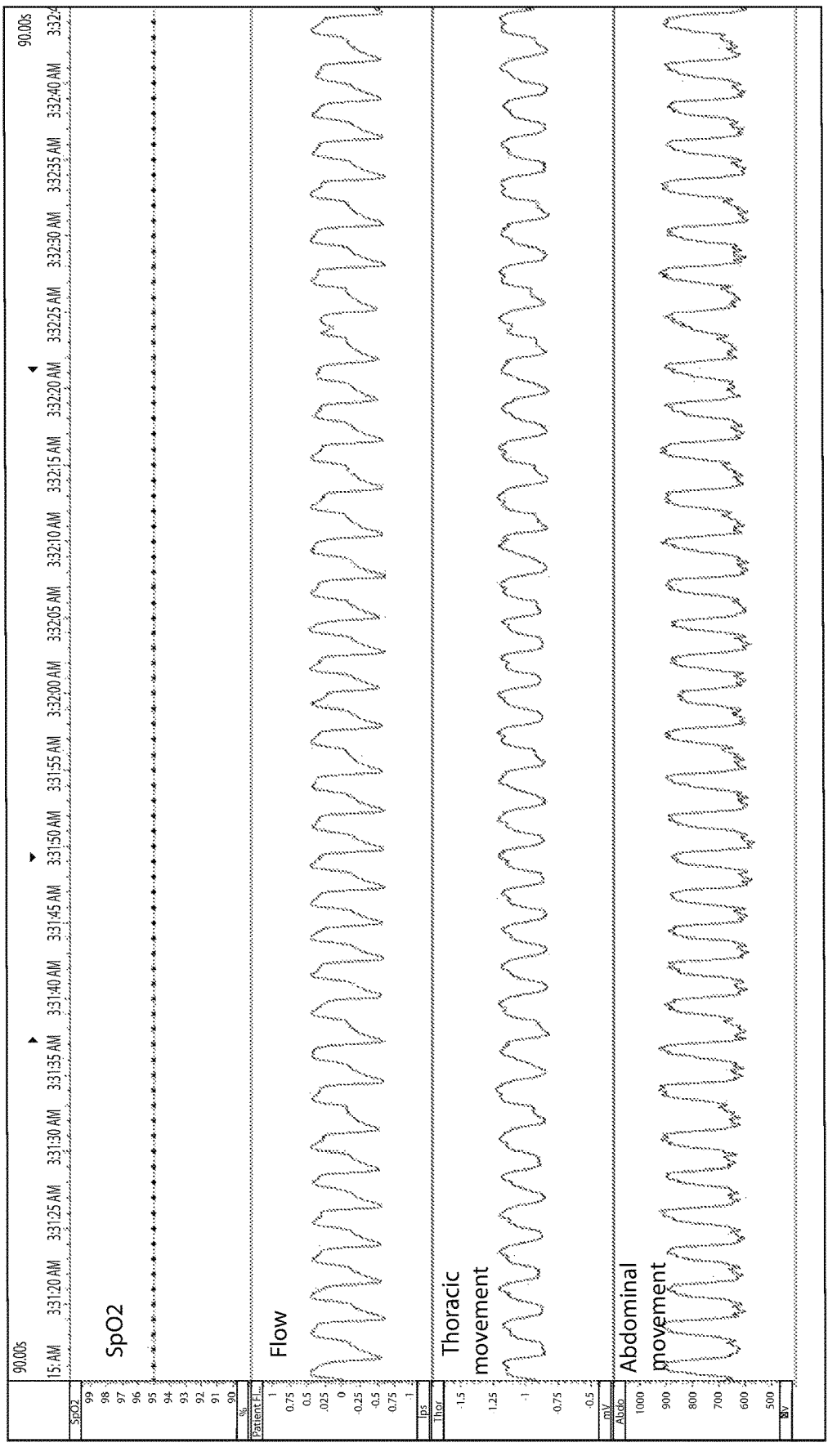

FIG. 6B shows selected polysomnography channels (pulse oximetry, flow rate, thoracic movement, and abdominal movement) of a patient during non-REM sleep breathing normally over a period of about ninety seconds.

Figure 6C:
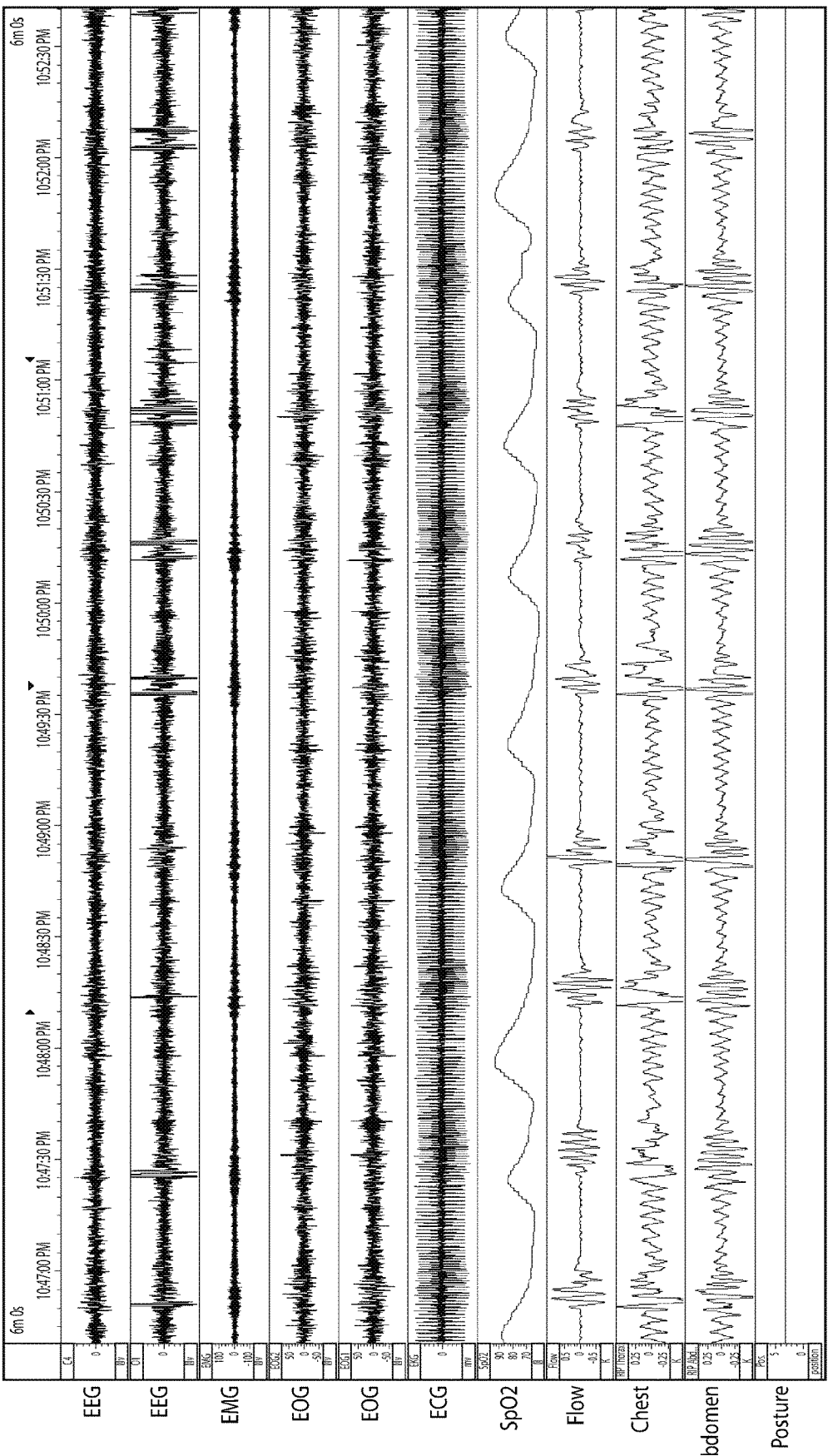

FIG. 6C shows polysomnography of a patient before treatment.

Figure 6D:
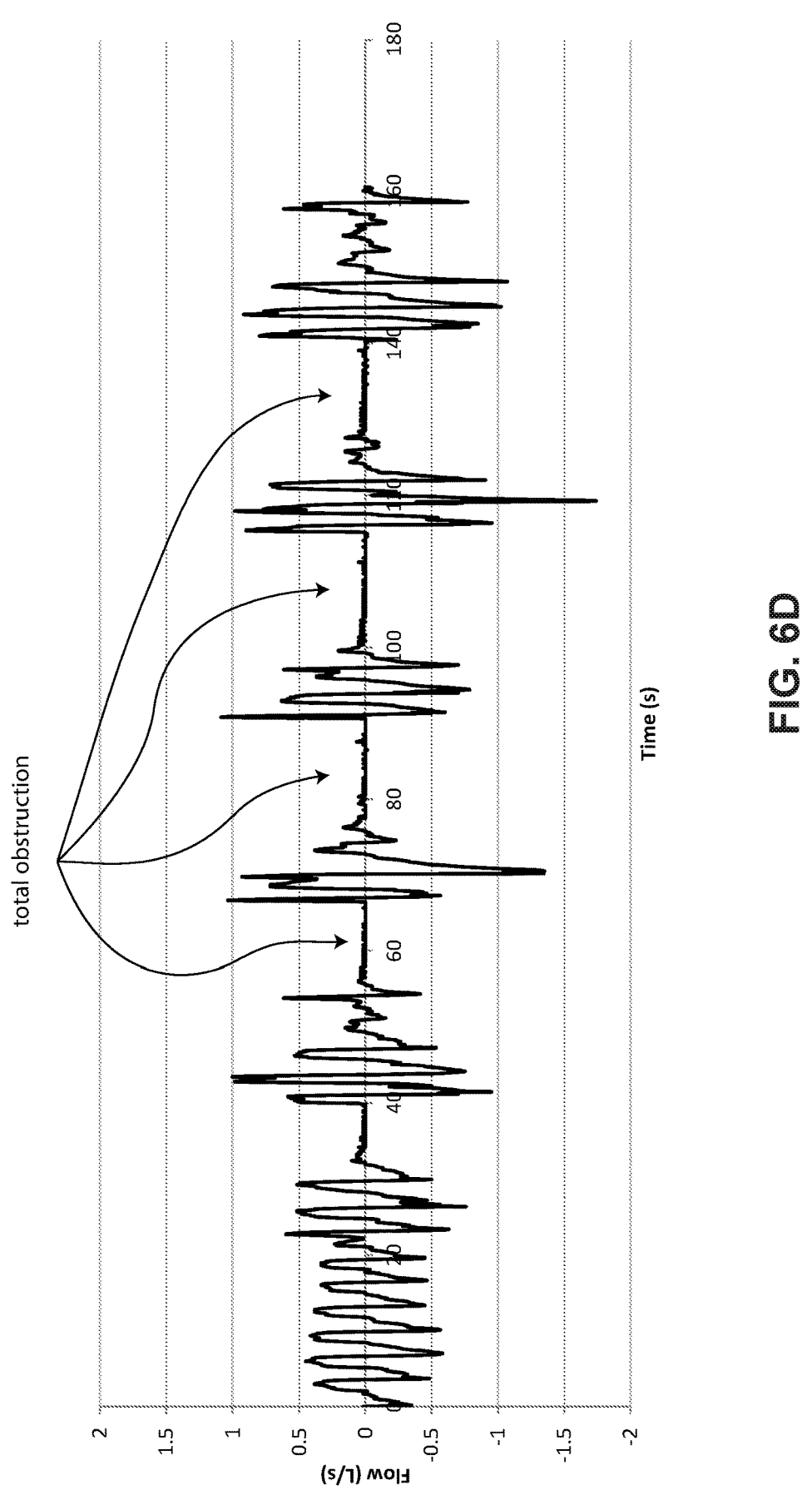

FIG. 6D shows patient flow rate data where the patient is experiencing a series of total obstructive apneas.

Figure 7:
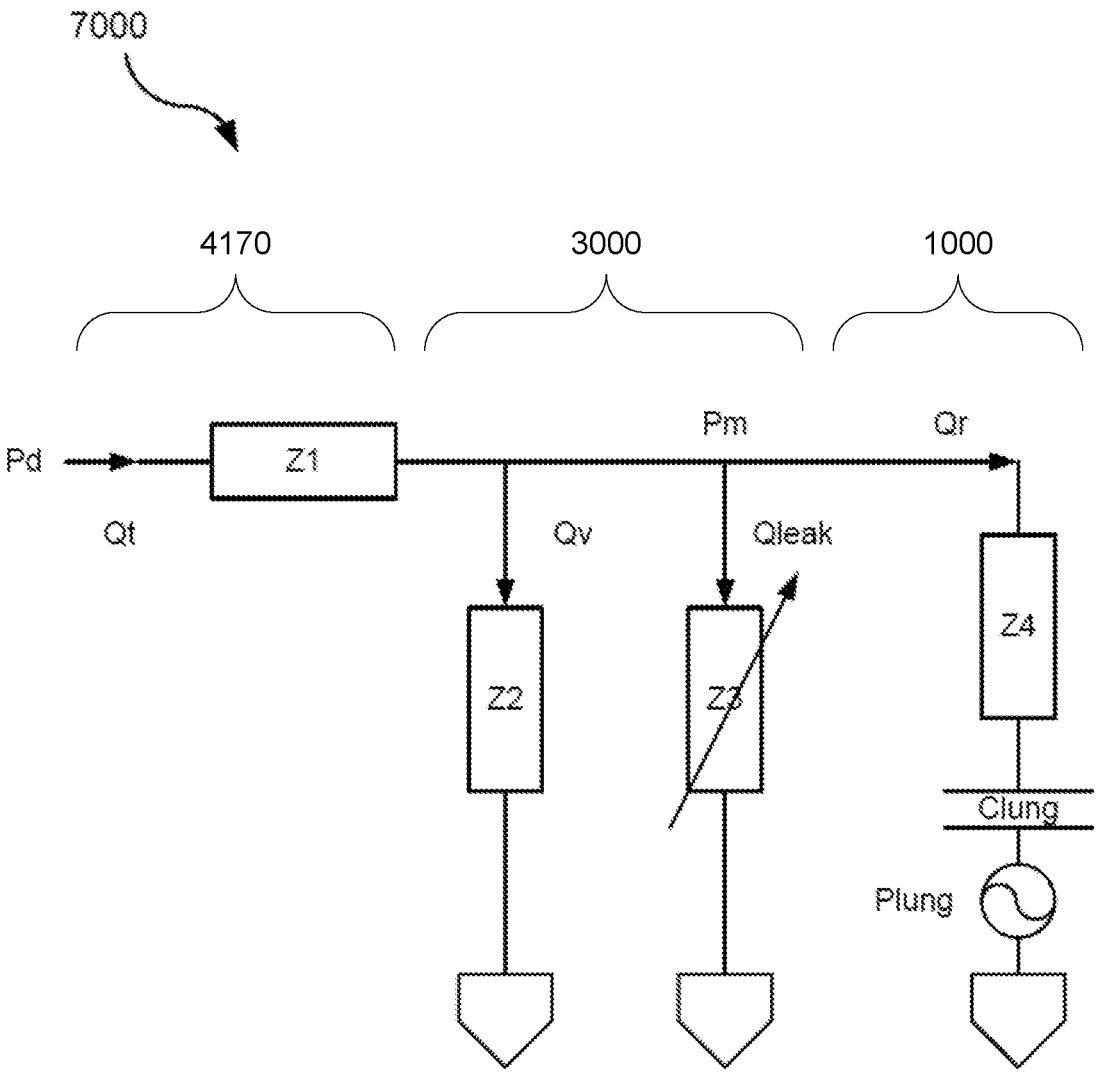

FIG. 7 is a schematic diagram of a model of the air circuit, patient interface, and patient in a respiratory pressure therapy system.

Figure 8:
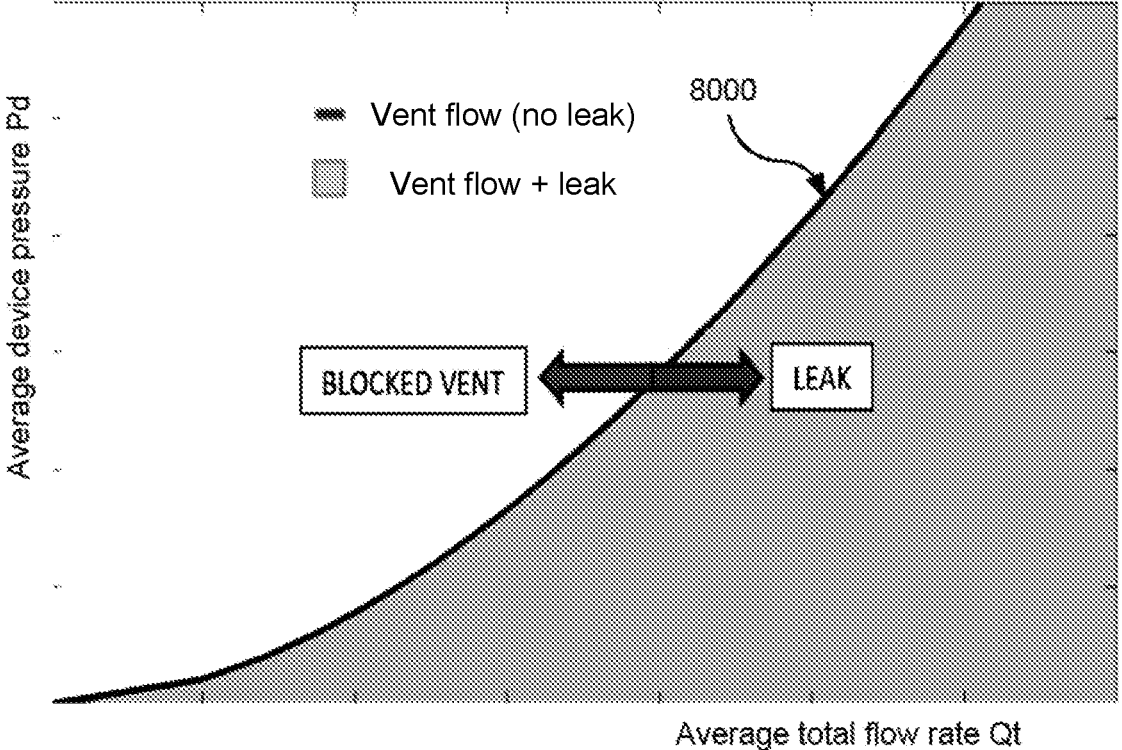

FIG. 8 contains an example graph of a curve relating average device pressure to average total flow rate in the absence of leak flow.

Figure 9:
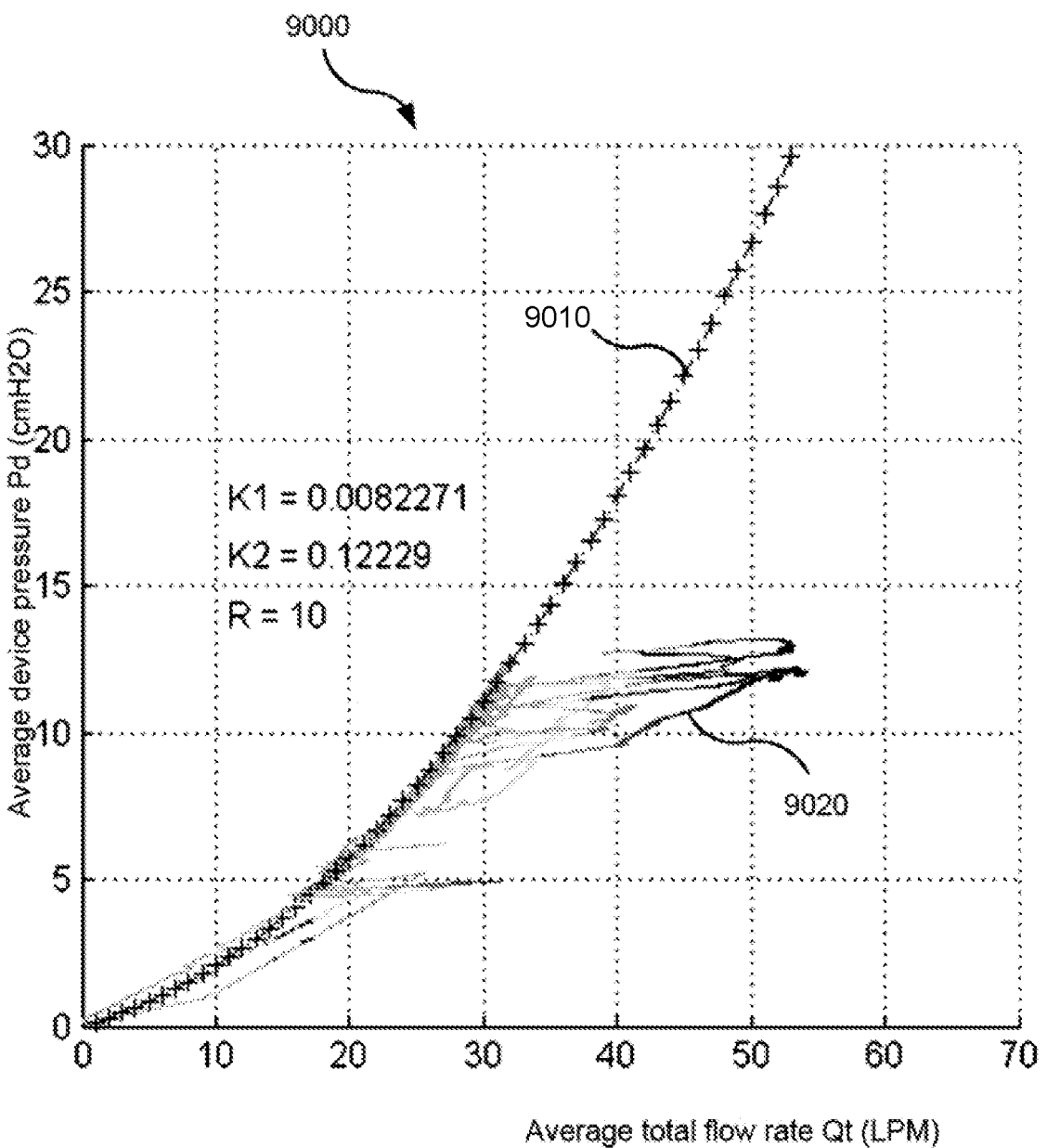

FIG. 9 contains a graph on which are plotted points representing average device pressure and average total flow rate over a period of APAP therapy.

Figure 10:
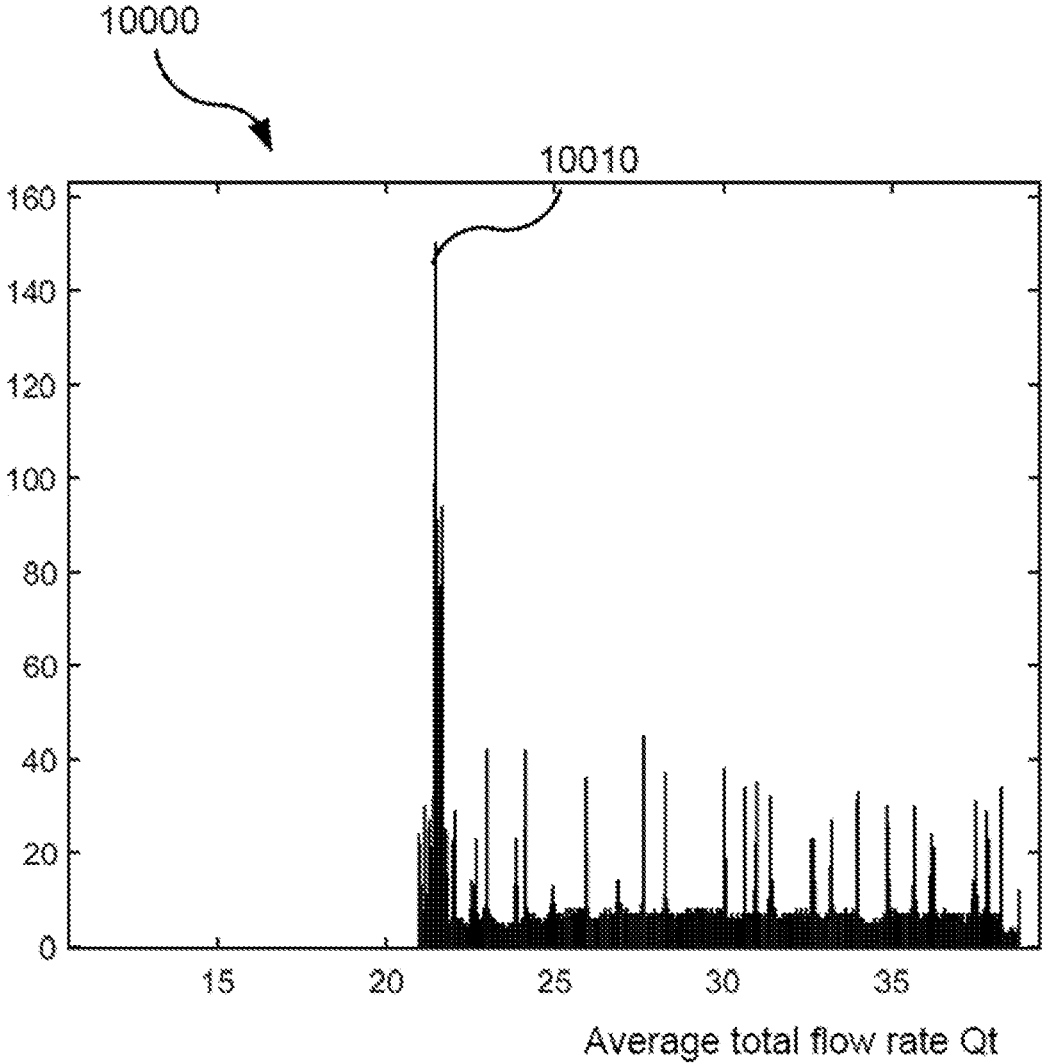

FIG. 10 is a histogram of values of average total flow rate for a given device pressure over a period of respiratory pressure therapy.

FIG. 11 contains a flow chart illustrating a method of characterising the respiratory therapy system according to one form of the present technology.

Figure 12:
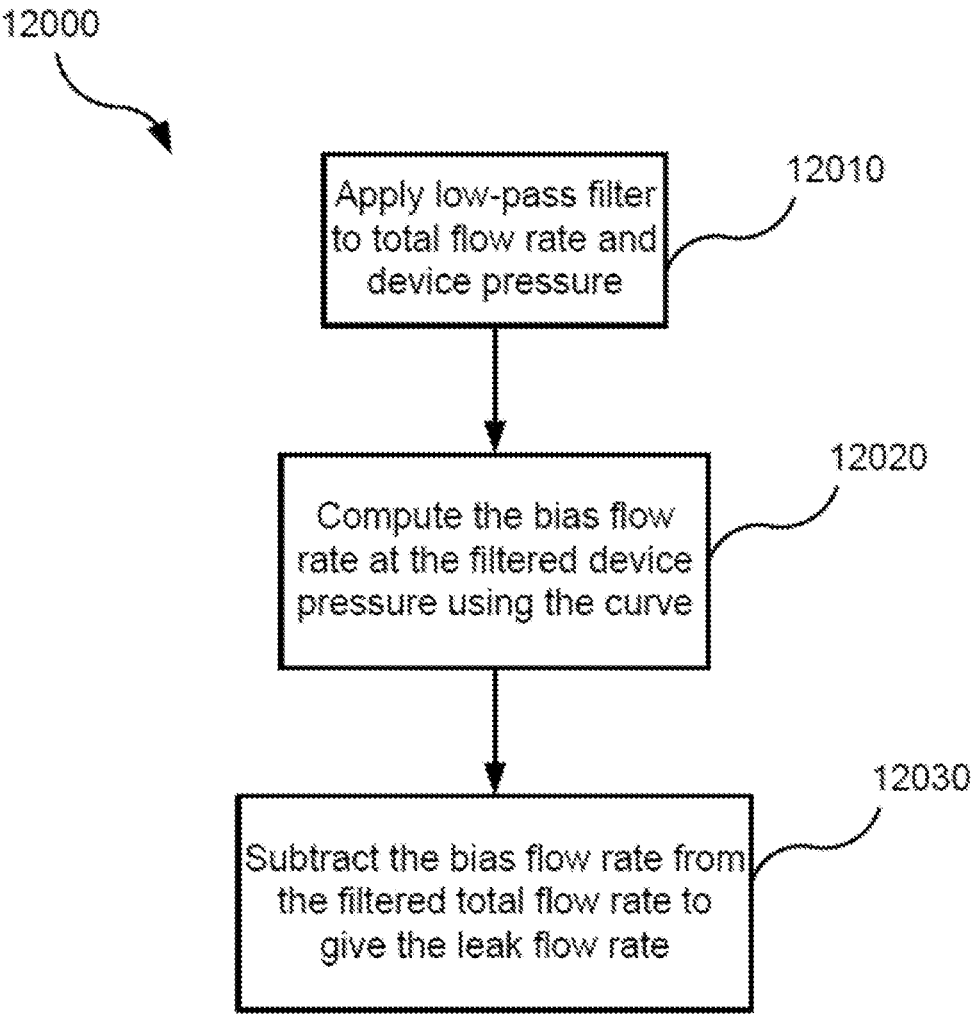

FIG. 12 contains a flow chart illustrating a method of estimating a leak flow rate according to one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

The present technology may be applied to a method for treating a respiratory disorder such as with control of applying positive pressure to the entrance of the airways of a patient 1000.

5.2 Respiratory Therapy Systems

The present technology may be applied to a respiratory therapy system for treating a respiratory disorder. A respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

5.3.1 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.4 Air Circuit

An air circuit 4170 in accordance with an aspect of the present technology is a conduit or a tube constructed and arranged to allow, in use, a flow of air to travel between two components such as RPT device 4000 and the patient interface 3000 or In particular, the air circuit 4170 may be in fluid connection with the outlet of the pneumatic block 4020 and the patient interface 3000. The air circuit may be referred to as an air delivery tube.

5.4.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000 or 3800.

5.5 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.5.1 RPT Device Mechanical & Pneumatic Components

An RPT device may comprise one or more of the following components in an integral unit. In an alternative form, one or more of the following components may be located as respective separate units.

5.5.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.5.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.5.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$ when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.5.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.5.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate of the flow of air is received by the central controller 4230.

5.5.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 and representing a pressure of the flow of air is received by the central controller 4230.

5.5.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.5.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.5.2 RPT Device Electrical Components

5.5.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.5.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.5.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5.2.4 Clock

The RPT device 4000 may include a clock 4232 that is connected to the central controller 4230.

5.5.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.5.2.6 Protection Circuits

The one or more protection circuits 4250 in accordance with the present technology may comprise an electrical protection circuit, a temperature and/or pressure safety circuit.

5.5.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.5.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.5.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.5.2.9.1 Display Driver

A display driver 4292 receives as an input the characters, symbols, or images intended for display on the display 4294, and converts them to commands that cause the display 4294 to display those characters, symbols, or images.

5.5.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 may be generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.5.3.1 Therapy System Characterisation

In one form of the present technology, a therapy system characterisation algorithm 4305 receives as input data representing:

a signal from the pressure sensor 4272 representative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd).

and generates a pressure-flow curve that is characteristic of the respiratory therapy system.

The therapy system characterisation algorithm 4305 is configured to operate on data that has been accumulated from the transducers 4270 over a period of therapy where provided pressure may change, such as an APAP therapy session. The period should be long enough to include a substantial range of device pressures, e.g. a range of at least 3 cmH$_2$O. In some implementations, the period is a full therapy session, but in other implementations one or two hours may be long enough to accumulate sufficient data. In some implementations, the early portion of the therapy period is discarded. In some implementations, the data corresponding to the lower portion of the pressure range is weighted more heavily in the analysis, since leak is more likely to occur at higher pressures. Accordingly, in some implementations, the system may perform a check, such as with time of use and/or with the measured pressure values to ensure sufficient pressure values of the desired range are accumulated for the computing of the pressure-flow characteristic curve (e.g., a best fit computation of one or more curve parameters).

The therapy system characterisation algorithm 4305 may be iterated once, or multiple times. In the latter case the therapy system characterisation algorithm 4305 may refine its estimate of the characteristic pressure-flow curve for the respiratory therapy system at each iteration.

FIG. 7 is a schematic diagram of a model 7000 of the air circuit 4170, patient interface 3000, and patient 1000 downstream of the delivery point of supplementary gas 4180. The impedance $Z_1$ represents the air circuit 4170 and causes a pressure drop $\Delta P$ that is a function of the total flow rate $Q$ t. The interface pressure Pm is the device pressure Pd less the pressure drop $\Delta P$ through the air circuit:

$$Pm = Pd - \Delta P(Q t) \tag{1}$$

where $\Delta P(Q)$ is the pressure drop characteristic of the air circuit 4170.

The impedance $Z_2$ represents the vent 3400. The vent flow $Q$ v is related to the interface pressure Pm via the vent characteristic $f$:

$$Pm = f(Qv) \tag{2}$$

Combining (1) with (2), the device pressure Pd may be written as $$Pd = f(Qv) + \Delta P(Q t) \tag{3}$$

The impedance $Z_3$ represents leak, which is unknown and unpredictably variable. The impedance $Z_4$, the capacitance Clung and the variable pressure source Plung represent characteristics of the patient.

It may be seen from the model 7000 that the total flow rate $Q$ t is equal to the sum of the vent flow rate $Q$ v, the leak flow rate $Q$ leak, and the respiratory flow rate $Q$ r:

$$Q t = Q v + Q \text{ leak} + Q r \tag{4}$$

The respiratory flow rate $Q$ r averages to zero over many respiratory cycles, since the average flow into or out of the lungs must be zero, so taking an average of each flow rate over many respiratory cycles, the vent flow rate may be approximated as $$\tilde{Q}v = \tilde{Q}t - \tilde{Q}\text{leak} \tag{5}$$

where the tilde (~) indicates averaging over many respiratory cycles. Averaging may be implemented by low-pass filtering with a time constant long enough to contain many respiratory cycles. In some implementations, the time constant is ten seconds, however other time constants are contemplated.

Combining equations (3) and (5), the average device pressure $\tilde{P}d$ may be written as $$\tilde{P}d=f(\tilde{Q}t-\tilde{Q}leak)+\Delta P(\tilde{Q}t) \tag{6}$$

Absent any leak flow ($Q$ leak==0), the average total flow rate $\tilde{Q}t$ may be referred to as the bias flow rate $Q$ b. Equation (6) gives a relationship between bias flow rate $Q$ b and average device pressure $\tilde{P}d$ that characterises the respiratory therapy system:

$$\tilde{P}d=f(Q\,b)+\Delta P(Q\,b) \tag{7}$$

The relationship, known as the pressure-flow curve for the system, is determined by the vent characteristic $f(Q)$ and the air circuit pressure drop characteristic $\Delta P(Q)$.

FIG. 8 contains an example graph of a pressure-flow curve 8000 representing average device pressure $\tilde{P}d$ as a function of average total flow rate $\tilde{Q}t$. The function can serve as an analytical tool for leak detection and/or vent blockage detection. Over a period of APAP therapy, as the average device pressure $\tilde{P}d$ varies, and absent any leak or vent blockage, the point ($\tilde{Q}t$, $\tilde{P}d$) will move up and down the pressure-flow curve 8000. Initiation of a leak will cause the point ($\tilde{Q}t$, $\tilde{P}d$) to move to the right of the pressure-flow curve 8000 for a period, and the resolution of the leak will return the point to the pressure-flow curve 8000. Thus, leak shows up as excursions to the right of the pressure-flow curve 8000, i.e. as points ($\tilde{Q}t$, $\tilde{P}d$) in which $\tilde{Q}t$ is greater than the bias flow $Q$ b at that value of average device pressure $\tilde{P}d$, as modelled by the pressure-flow curve 8000. Vent blockage shows up as excursions to the left of the pressure-flow curve 8000, i.e. points ($\tilde{Q}t$, $\tilde{P}d$) in which $\tilde{Q}t$ is less than the bias flow $Q$ b at that value of average device pressure $\tilde{P}d$. Vent blockages can occur, for example, as a result of the patient's head movement relative to the pillow they are sleeping on.

In one implementation, the pressure-flow curve for a respiratory pressure therapy system may be approximated by a function such as a quadratic:

$$\tilde{P}_d=k_1 Q_b{}^2+k_2 Q_b \tag{8}$$

The parameters of the pressure-flow curve, in this quadratic implementation $k_1$ and $k_2$, characterise the series concatenation of the vent characteristic $f$ and the air circuit pressure drop characteristic $\Delta P$.

If the air circuit pressure drop characteristic $\Delta P(Q)$ is known, e.g. because the type of conduit making up the air circuit 4170 is known, or through a prior calibration operation, then the parameters of the pressure-flow curve effectively characterise the vent 3400, which in turn is indicative of the type of patient interface 3000. The therapy system characterisation algorithm 4305, in these circumstances, may therefore be used to identify the patient interface 3000. In one implementation, this may be done by comparing the computed curve parameters (e.g., $k_1$ and $k_2$) to a data structure such as an array or database having such parameters (e.g., parameter pairs ($k_1$, $k_2$)) associated with known patient interface types when used with the known conduit. The type of patient interface associated with the stored parameters (e.g., pair ($k_1$, $k_2$)) that most closely matches the computed parameters (e.g., $k_1$ and $k_2$) may be taken as the type of the patient interface 3000. Alternatively, the pressure drop $\Delta P(\tilde{Q}t)$ may be subtracted from each value of the average device pressure $\tilde{P}d$ before fitting the function (e.g., quadratic) to the resulting mask pressure-flow curve. The resulting parameters that are determined (e.g., $k_1$ and $k_2$) may then be compared to a data structure of parameters (e.g., pairs ($k_1$, $k_2$)) associated with known patient interface types to identify the patient interface 3000 or access data for operations of the RPT device that is associated with use of particular patient interfaces.

FIG. 9 contains a graph 9000 on which are plotted points ($\tilde{Q}t$, $\tilde{P}d$) over a period of APAP therapy. The crosses (+) trace out a pressure-flow curve 9010 relating each value of average device pressure $\tilde{P}d$ to the bias flow rate $Q$ b at that value of device pressure. The excursions, e.g. data points 9020, to the right of the curve 9010 result from leaks being initiated and resolved.

FIG. 10 is a histogram 10000 of values of average total flow rate $\tilde{Q}t$ for a given average device pressure $\tilde{P}d$ over a period of respiratory pressure therapy. The histogram 10000 has a peak value 10010 whose value of average total flow rate $\tilde{Q}t$ may be taken as the bias flow rate $Q$ b for the given average device pressure $\tilde{P}d$, on the reasonable assumption that the most common leak value for a well-fitted mask is zero, and therefore the bias flow rate $Q$ b is the mode (most common value) of the histogram of average total flow rate $\tilde{Q}t$. The values of average total flow rate $\tilde{Q}t$ in excess of the bias flow rate $Q$ b represent leak flows. The values of average total flow rate $\tilde{Q}t$ below the bias flow rate $Q$ b represent vent blockages.

FIG. 11 contains a flow chart illustrating an example method 11000 that may be carried out to implement the therapy system characterisation algorithm 4305. The method 11000 may start at step 11010, which applies a filter such as a low-pass filter with a time constant of many respiratory cycles to the data representing the signal from the pressure sensor 4272 representative of the device pressure Pd, to obtain a filtered device pressure $\tilde{P}d$. The step 11010 also computes the total flow rate $Q$ t as the device flow rate $Q$ d, optionally plus the flow rate of any supplementary gas 4180, and applies a filter, such as a low-pass filter, e.g. the same low-pass filter as previously mentioned, to the total flow rate $Q$ t to obtain a filtered total flow rate $\tilde{Q}t$.

Step 11020 forms a histogram of values of filtered total flow rate $\tilde{Q}t$ at each value of filtered device pressure $\tilde{P}d$. Step 11020 then finds the bias flow rate $Q$ b from the histogram for each value of filtered device pressure $\tilde{P}d$. A determination of such a bias flow rate value from each histogram may, for example, involve a determination of a peak of the histogram data or a determination of the bin (e.g., a certain filtered total flow rate value) with the highest number of counts (e.g., repeated occurrences) in the histogram.

The next step 11030 fits a pressure-flow curve to the points ($Q_b$, $\tilde{P}_d$), a step which comprises finding or computing parameters of a template curve that most closely fit the curve to the set of points ($Q_b$, $\tilde{P}_d$). In one implementation, the template curve is of the quadratic form of equation (8), so the curve fitting comprises computing the parameters $k_1$ and $k_2$ that most closely fit the quadratic form to the set of points ($Q_b$, $\tilde{P}_d$). In one implementation, least-squares fitting is used to compute the best-fit parameters of the curve.

At an optional final step 11040, the method 11000 may compare the determined parameters of the best-fit curve to sets of parameters stored in a database or other suitable data structure. Each set of parameters in the database/data structure may be associated with a particular type of patient interface. This comparison identifies the set of parameters that most closely matches the parameters computed in step 11030. The type of patient interface in the database/data structure that is associated with the set of parameters that most closely matches the computed parameters may be taken as the identified type of the patient interface 3000.

Optionally, with such an identification, parameter(s) of operation of the RPT device may be adjusted, by its controller, based on accessed data that is associated with the most closely matched set of parameters, as described herein. For example, a flow or pressure therapy control parameter, such as for operation of the blower, may be adjusted based on the identification. Optionally, such an adjusted control parameter may thereafter be applied by the RPT device so as to operate the blower to provide any respiratory therapy described herein based on the adjusted control parameter.

5.5.3.2 Pre-Processing Module

For example, a pre-processing module 4310 in accordance with one form of the present technology receives as an input a signal from a transducer 4270, for example a flow rate sensor 4274 or pressure sensor 4272, and optionally the pressure-flow curve parameters estimated by the system characterisation algorithm 4305, and performs one or more process steps to calculate one or more output values that will be used as an input to another module, for example a therapy engine module 4320. The pre-processing module 4310 is therefore carried out during therapy with minimal latency between input signals and output signals.

In one implementation of the present technology, the output values include the interface pressure Pm, the vent flow rate $Q$ v, the respiratory flow rate $Q$ r, and the leak flow rate $Q$ l.

In various implementation of the present technology, the pre-processing module 4310 comprises one or more of the following algorithms: interface pressure estimation 4312, vent flow rate estimation 4314, leak flow rate estimation 4316, and respiratory flow rate estimation 4318.

5.5.3.2.1 Interface Pressure Estimation

In one implementation of the present technology, an interface pressure estimation algorithm 4312 receives as inputs a signal from the pressure sensor 4272 representative of the pressure in the pneumatic path proximal to an outlet of the pneumatic block (the device pressure Pd) and a signal from the flow rate sensor 4274 representative of the flow rate of the airflow leaving the RPT device 4000 (the device flow rate $Q$ d) and provides as an output an estimated pressure, Pm, in the patient interface 3000.

In one implementation, the interface pressure estimation algorithm 4312 first computes the total flow rate $Q$ t as the device flow rate $Q$ d plus the flow rate of any supplementary gas 4180. The interface pressure estimation algorithm 4312 then applies equation (1) to estimate the interface pressure Pm as the device pressure Pd minus the air circuit pressure drop ΔP at the total flow rate $Q$ t, using the pressure drop characteristic ΔP($Q$) of the air circuit 4170.

Optionally, with such an estimation, parameter(s) of operation of the RPT device may be adjusted, by its controller, based on the estimation. For example, a flow or pressure therapy control parameter, such as for operation of the blower, may be adjusted based on the estimation. Optionally, such an adjusted control parameter may thereafter be applied by the RPT device so as to operate the blower to provide any respiratory therapy described herein based on the adjusted control parameter.

5.5.3.2.2 Vent Flow Rate Estimation

In one implementation of the present technology, a vent flow rate estimation algorithm 4314 receives as an input an estimated pressure, Pm, in the patient interface 3000 from the interface pressure estimation algorithm 4312 and estimates a vent flow rate of air, $Q$ v, from the vent 3400 in the patient interface 3000. The relationship between the vent flow rate $Q$ v and the interface pressure Pm for the particular vent 3400 in use is modelled by the vent characteristic $f$ of equation (2), which may be provided by the system characterisation algorithm 4305 from its knowledge of the type of patient interface 3000 in use.

Optionally, with such an estimation, parameter(s) of operation of the RPT device may be adjusted, by its controller, based on the estimation. For example, a flow or pressure therapy control parameter, such as for operation of the blower, may be adjusted based on the estimation. Optionally, such an adjusted control parameter may thereafter be applied by the RPT device so as to operate the blower to provide any respiratory therapy described herein based on the adjusted control parameter.

5.5.3.2.3 Leak Flow Rate Estimation

In one implementation of the present technology, a leak flow rate estimation algorithm 4316 receives as an input the total flow rate $Q$ t from the interface pressure estimation algorithm 4312, the vent flow rate $Q$ v from the vent flow rate estimation algorithm 4314, and provides as an output an estimate of the leak flow rate $Q$ l.

In one implementation, the leak flow rate estimation algorithm 4316 estimates the leak flow rate $Q$ l by calculating a filtered version (e.g., a low-pass filtered version) of the non-vent flow rate (equal to the difference between the total flow rate $Q$ t and the vent flow rate $Q$ v from the vent flow rate estimation algorithm 4314). The time constant of the low-pass filter is sufficiently long to include several respiratory cycles.

In one implementation, the leak flow rate estimation algorithm 4316 receives as an input the total flow rate $Q$ t, the vent flow rate $Q$ v, and the estimated pressure Pm in the patient interface 3000 from the interface pressure estimation algorithm 4312, and provides as an output a leak flow rate $Q$ l, by calculating a leak conductance, and determining the leak flow rate $Q$ l to be a function of leak conductance and interface pressure Pm. Leak conductance may be calculated as the quotient of low pass filtered non-vent flow rate and low-pass filtered square root of interface pressure Pm, where the low-pass filter time constant has a value sufficiently long to include several respiratory cycles. The leak flow rate $Q$ l may be estimated as the product of leak conductance and a function, e.g. the square root, of interface pressure Pm.

In one implementation, the leak flow rate estimation algorithm 4316 receives as an input the total flow rate $Q$ t and the device pressure Pd, and provides as an output an estimate of the leak flow rate $Q$ l. FIG. 12 contains a flow chart illustrating a method 12000 of estimating a leak flow rate $Q$ l according to this implementation. The method 12000 may be used to implement the leak flow rate estimation algorithm 4316 in one implementation of the present technology.

The method 12000 starts at step 12010, which applies a filter such as a low-pass filter with a time constant of many respiratory cycles to the device pressure Pd, to obtain a filtered device pressure P̃d. The step 12010 also computes the total flow rate $Q$ t as the device flow rate $Q$ d, optionally plus the flow rate of any supplementary gas 4180, and applies a filter, such as a low-pass filter, e.g. the same low-pass filter as previously mentioned, to the total flow rate $Q$ t to obtain a filtered total flow rate $Q$ t.

The next step 12020 finds the bias flow rate $Q$ b at the current filtered device pressure P̃d using the pressure-flow curve parameters provided by the system characterisation algorithm 4305. Step 12020 may involve inverting the pressure-flow curve to find the bias flow rate $Q$ b at the current filtered device pressure P̃d. This may be done analytically in the implementations of the technology in which the pressure-flow curve is a quadratic, as in equation (8). Alternatively, a lookup table may be created by the system characterisation algorithm 4305, in which values of bias flow rate $Q$ b are tabulated against values of device pressure $\hat{P}$d computed using the pressure-flow curve. Step 12020 may then make use of the lookup table to find the bias flow rate $Q$ b.

Step 12020 then subtracts the bias flow rate $Q$ b from the filtered total flow rate $Q$ t to obtain an estimate of the leak flow rate $Q$ l.

Optionally, with such an estimation, parameter(s) of operation of the RPT device may be adjusted, by its controller, based on the estimation. For example, a flow or pressure therapy control parameter, such as for operation of the blower, may be adjusted based on the estimation. Optionally, such an adjusted control parameter may thereafter be applied by the RPT device so as to operate the blower to provide any respiratory therapy described herein based on the adjusted control parameter.

5.5.3.2.4 Respiratory Flow Rate Estimation

In one implementation of the present technology, a respiratory flow rate estimation algorithm 4318 receives as an input the total flow rate $Q$ t, the vent flow rate $Q$ v, and the leak flow rate $Q$ l, and estimates a respiratory flow rate $Q$ r by subtracting the vent flow rate $Q$ v and the leak flow rate $Q$ l from the total flow rate $Q$ t.

It may be seen that accurate knowledge of the therapy system pressure-flow characteristic curve, as provided by the therapy system characterisation algorithm 4305, ripples through to accurate estimation of leak flow rate, vent flow rate, and respiratory flow rate by the algorithms of the pre-processing module 4310, with consequent benefits to the efficacy of the respiratory therapy. The therapy engine module 4320 benefits in particular from accurate estimation of the respiratory flow rate $Q$ r.

For example, with such an estimation, parameter(s) of operation of the RPT device may be adjusted, by its controller, based on the estimation. For example, a flow or pressure therapy control parameter, such as for operation of the blower, may be adjusted based on the estimation. Optionally, such an adjusted control parameter may thereafter be applied by the RPT device so as to operate the blower to provide any respiratory therapy described herein based on the adjusted control parameter.

5.5.3.3 Therapy Engine Module

In one form of the present technology, a therapy engine module 4320 receives as inputs one or more of a pressure, Pm, in a patient interface 3000, and a respiratory flow rate of air to a patient, $Q$ r, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.5.3.3.1 Phase Determination

In one form of the present technology, the RPT device 4000 does not determine phase.

In one form of the present technology, a phase determination algorithm 4321 receives as an input a signal representative of respiratory flow rate, $Q$ r, and provides as an output a phase $\Phi$ of a current respiratory cycle of a patient 1000.

In some forms, known as discrete phase determination, the phase output $\Phi$ is a discrete variable. One implementation of discrete phase determination provides a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output $\Phi$ is determined to have a discrete value of 0 (thereby "triggering" the RPT device 4000) when the respiratory flow rate $Q$ r has a value that exceeds a positive threshold, and a discrete value of 0.5 revolutions (thereby "cycling" the RPT device 4000) when a respiratory flow rate $Q$ r has a value that is more negative than a negative threshold. The inhalation time Ti and the exhalation time Te may be estimated as typical values over many respiratory cycles of the time spent with phase $\Phi$ equal to 0 (indicating inspiration) and 0.5 (indicating expiration) respectively.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, the phase $\Phi$ is first discretely estimated from the respiratory flow rate $Q$ r as described above, as are the inhalation time Ti and the exhalation time Te. The continuous phase $\Phi$ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.5.3.3.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.5.3.3.3 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Q r and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty-five scaled data points are generated by the central controller 4230, and represent a moving average of the preceding several inspiratory events, e.g., three events. The moving average of continuously updated values of the (e.g., sixty-five) points are hereinafter called the "scaled flow rate", designated as Q s(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty-two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.5.3.3.4 Determination of apneas and hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Q r and provides as an output a flag that indicates that an apnea or a hypopnea has been detected.

In one form, an apnea will be said to have been detected when a function of respiratory flow rate Q r falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Q r falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.5.3.3.5 Determination of Snore

In one form of the present technology, the central controller 4230 executes one or more snore determination algorithms 4326 for the determination of the extent of snore.

In one form, the snore determination algorithm 4326 receives as an input a respiratory flow rate signal $Q$ r and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal $Q$ r to reduce background noise, e.g., the sound of airflow in the system from the blower.

5.5.3.3.6 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal $Q$ r, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal $Q$ r, and determines the presence or absence of a cardiogenic signal. The absence of a cardiogenic signal is taken to be an indication of a closed airway.

5.5.3.3.7 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.5.3.4 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 is equal to the treatment pressure Pt.

5.5.3.5 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)

Transducer fault detection

Failure to detect the presence of a component

Operating parameters outside recommended ranges (e.g. pressure, flow rate, temperature, PaO$_2$)

Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm

Sending a message to an external device

Logging of the incident

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6s, peak inspiratory flow rate $Q$ peak 0.4 L/s, exhalation time Te 2.4s, peak expiratory flow rate $Q$ peak –0.5 L/s. The total duration of the breath, Ttot, is about 4s. The person typically breathes at a rate of about 15 breaths per minute (BPM), with Ventilation Vent about 7.5 L/min. A typical duty cycle, the ratio of Ti to Ttot, is about 40%.

FIG. 6B shows selected polysomnography channels (pulse oximetry, flow rate, thoracic movement, and abdominal movement) of a patient during non-REM sleep breathing normally over a period of about ninety seconds, with about 34 breaths, being treated with automatic PAP therapy, and the interface pressure being about 11 $cmH_2O$. The top channel shows pulse oximetry (oxygen saturation or $SpO_2$), the scale having a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electocardiogram. The seventh channel shows pulse oximetry ($SpO_2$) with repetitive desaturations to below 70% from about 90%. The eighth channel is respiratory airflow using a nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow rate data where the patient is experiencing a series of total obstructive apneas. The duration of the recording is approximately 160 seconds. Flow rates range from about +1 L/s to about −1.5 L/s. Each apnea lasts approximately 10-15s.

5.8 Respiratory Therapy Modes

Various respiratory therapy modes may be implemented by the disclosed respiratory therapy system.

5.8.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$.

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 $cmH_2O$ and 25 $cmH_2O$ respectively. In other implementations, the pressure increment $\Delta P$ can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$−Pmin, so that the decrease in $P_0$ to the minimum treatment pressure Pmin in the absence of any detected events is exponential. In one implementation, the constant of proportionality is set such that the time constant $\tau$ of the exponential decrease of $P_0$ is 60 minutes, and the minimum treatment pressure Pmin is 4 $cmH_2O$. In other implementations, the time constant $\tau$ could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in $P_0$ could be predetermined, so the decrease in $P_0$ to the minimum treatment pressure Pmin in the absence of any detected events is linear.

5.8.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000.

That is, based on the typical waveform templates $\Pi(\Phi, t)$ described above, the therapy parameter determination algorithm 4329 increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few $cmH_2O$) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol $Q$. 'Flow rate' is sometimes shortened to simply 'flow' or 'airflow'.

In the example of patient respiration, a flow rate may be nominally positive for the inspiratory portion of a respiratory cycle of a patient, and hence negative for the expiratory portion of the respiratory cycle of a patient. Device flow rate, $Q$ d, is the flow rate of air leaving the RPT device. Total flow rate, $Q$ t, is the flow rate of air and any supplementary gas reaching the patient interface via the air circuit. Vent flow rate, $Q$ v, is the flow rate of air leaving a vent to allow washout of exhaled gases. Leak flow rate, $Q$ l, is the flow rate of leak from a patient interface system or elsewhere. Respiratory flow rate, $Q$ r, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: An unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a respiratory cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the respiratory cycle it may be described as inspiratory flow limitation. Where flow limitation occurs during an expiratory portion of the respiratory cycle it may be described as expiratory flow limitation.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal.

Inspiratory portion of a respiratory cycle: The period from the start of inspiratory flow to the start of expiratory flow will be taken to be the inspiratory portion of a respiratory cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate ($Q$ peak): The maximum value of flow rate during the inspiratory portion of the respiratory flow waveform.

Respiratory flow rate, patient airflow rate, respiratory airflow rate ($Q$ r): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

5.11 Reference Signs List patient 1000
bed partner 1100
patient interface 3000
seal—forming structure 3100
plenum chamber 3200
structure 3300
vent 3400
connection port 3600
forehead support 3700
RPT device 4000
external housing 4010
upper portion 4012
portion 4014
panels 4015 chassis 4016
handle 4018
pneumatic block 4020
air filters 4110
inlet air filter 4112
outlet air filter 4114
mufflers 4120
inlet muffler 4122
outlet muffler 4124
pressure generator 4140
blower 4142
motor 4144
anti—spill back valve 4160
air circuit 4170
supplementary gas 4180
electrical components 4200
Printed Circuit Board Assembly 4202
power supply 4210
input devices 4220
central controller 4230
clock 4232
therapy device controller 4240
protection circuits 4250
memory 4260
transducers 4270
pressure sensor 4272
flow rate sensor 4274
motor speed transducer 4276
data communication interface 4280
remote external communication network 4282
local external communication network 4284
remote external device 4286
local external device 4288
output device 4290
display driver 4292
display 4294
algorithms 4300
system characterisation algorithm 4305
pre—processing module 4310
interface pressure estimation algorithm 4312
vent flow rate estimation algorithm 4314
leak flow rate estimation algorithm 4316
respiratory flow rate estimation algorithm 4318
therapy engine module 4320
phase determination algorithm 4321
waveform determination algorithm 4322
ventilation determination 4323
inspiratory flow limitation determination algorithm 4324
apnea/hypopnea determination algorithm 4325
snore determination algorithm 4326
airway patency determination algorithm 4327
target ventilation determination 4328
therapy parameter determination algorithm 4329
therapy control module 4330
methods 4340
method 4500
step 4520
step 4530
step 4540
step 4550
step 4560
humidifier 5000
humidifier inlet 5002
humidifier outlet 5004
humidifier base 5006
humidifier reservoir 5110 humidifier reservoir dock 5130
heating element 5240
model 7000
pressure—flow curve 8000
curve 9000
pressure—flow curve 9010
excursion 9020
histogram 10000
peak 10010
method 11000
step 11010
step 11020
step 11030
step 11040
method 12000
step 12020
step 12020
step 12030

The invention claimed is:

1. Apparatus for respiratory therapy, the apparatus comprising:
 a pressure generator configured to generate a flow of air to a patient interface for a respiratory therapy for a patient;
 a pressure transducer configured to generate a signal representing a pressure of the flow of air;
 a flow rate transducer configured to generate a signal representing a flow rate of the flow of air;
 a controller configured to:
  receive the pressure signal and the flow rate signal from the transducers;
  analyse the pressure signal and the flow rate signal to identify the patient interface; and
 a central controller of the pressure generator, the central controller configured to:
  receive the identification of the patient interface, and
  control the pressure generator to adjust a property of the flow of air based on the identification,
  wherein the analysis comprises a determination of parameters that best fit a template curve to a plurality of points, each point comprising: (a) a pressure value, and (b) a flow rate value at the pressure value.

2. The apparatus of claim 1, wherein the controller is the central controller of the pressure generator.

3. The apparatus of claim 1, wherein the controller is a processor of a remote external device in communication with the central controller of the pressure generator.

4. The apparatus of claim 1, wherein the central controller is configured to determine the identification of the patient interface based on the determination of parameters.

5. The apparatus of claim 1, wherein the central controller is configured to determine a control parameter for adjustment of the property of the flow of air.

6. The apparatus of claim 5, wherein the central controller is configured to adjust the control parameter based on the determination of the parameters.

7. The apparatus of claim 1, wherein the pressure value comprises a value of a low-pass filtered version of measured pressure from the pressure signal.

8. The apparatus of claim 7, wherein the flow rate value comprises a mode of a histogram of values of measured flow rate from the flow rate signal at the pressure value.

9. The apparatus of claim 8, wherein the controller is configured to determine the mode of the histogram of values, and wherein the histogram of values is a histogram of a low-pass filtered version of measured flow rate from the flow rate signal at the pressure value.

10. The apparatus of claim 1, wherein the controller is configured to subtract a pressure drop from a measured pressure value from the pressure signal for the analysing.

11. The apparatus of claim 10, wherein the pressure drop is a pressure drop of an air circuit connecting the apparatus to the patient interface at a measured flow rate from the flow rate signal.

12. The apparatus of claim 1, wherein the controller is configured to determine the plurality of points during a therapy session comprising automatic positive airway pressure (APAP) therapy.

13. The apparatus of claim 1, wherein the controller is configured to condition the analysis on checking of a time of therapy use and/or a range of provided therapy pressures of a therapy session.

14. The apparatus of claim 1, wherein the controller is configured to estimate a leak flow rate from measured pressure from the pressure signal, measured flow rate from the flow rate signal, and the determined parameters.

15. The apparatus of claim 14 wherein the controller is configured to determine a bias flow rate based on a pressure-flow curve defined by the determined parameters.

16. The apparatus of claim 15 wherein the controller is configured to determine the leak flow estimate by subtracting the bias flow rate from the measured flow rate, wherein the measured flow rate comprises a total flow rate.

17. The apparatus of claim 15, wherein the pressure-flow curve defined by the determined parameters comprises a quadratic function.

18. The apparatus of claim 15, wherein the controller is configured to determine the bias flow rate by inverting the pressure-flow curve defined by the determined parameters.

19. The apparatus of claim 14, wherein the controller is configured to estimate a respiratory flow rate of the patient from the measured flow rate, the measured pressure, the determined parameters, and the estimated leak flow rate.

20. The apparatus of claim 19, wherein to control the adjustment to the property of the flow of air, the central controller is configured to:
 detect an event from the estimated respiratory flow rate of the patient, and
 adjust a treatment pressure of the flow of air in response to the detected event.

21. The apparatus of claim 20, wherein the event is an event from the group consisting of: an apnea, a hypopnea, a snore, and inspiratory flow limitation.

22. The apparatus of claim 1, wherein the analysis further comprises:
 a comparison of the determined parameters with a plurality of sets of parameters in a database, and
 the identification of the patient interface based on the comparison of the determined parameters.

23. The apparatus of claim 1, wherein the template curve is a quadratic function.

24. The apparatus of claim 1, wherein the controller is configured to determine a vent blocking event based on the determined parameters.

25. The apparatus of claim 24 wherein the controller is configured to determine the vent blocking event based on comparing a measure of average total flow rate with a flow rate at a given device pressure according to a function comprising the determined parameters.

26. The apparatus of claim 25 wherein the controller is configured to generate an indication of the vent blocking event if the measure of average total flow rate is less than the flow rate according to the function.

27. A method of operating in a respiratory treatment apparatus that is configured to generate a flow of air to a patient interface for a respiratory therapy for a patient, the method comprising:

accessing data representing a measured pressure of the flow of air, the measured pressure generated using a pressure transducer;

accessing data representing a measured flow rate of the flow of air, the measured flow rate generated using a flow rate transducer;

analysing, in a controller, the measured pressure and the measured flow rate to identify the patient interface, wherein the analysing comprises determining parameters that best fit a template curve to a plurality of points, each point comprising: (a) a pressure value, and (b) a flow rate value at the pressure value; and control adjusting a property of the flow of air based on the identification.

28. The method of claim 27 wherein the controller determines the identification of the patient interface based on the determining of parameters.

29. The method of claim 27, further comprising controlling, in the controller, a determination of a value of a control parameter for operating a pressure generator of the respiratory treatment apparatus based on the identification of the patient interface.

30. The method of claim 27, further comprising deriving the pressure value by low-pass filtering the measured pressure.

31. The method of claim 30, further comprising determining the flow rate value by deriving a histogram of values of the measured flow rate at the pressure value and determining a mode of the histogram.

32. The method of claim 31, wherein deriving the histogram comprises determining values of a low-pass filtered version of the measured flow rate at the pressure value.

33. The method of claim 27, further comprising subtracting a pressure drop value from the measured pressure for the analysing.

34. The method of claim 33, wherein the pressure drop value represents a pressure drop of an air circuit connecting the respiratory treatment apparatus to the patient interface at the measured flow rate.

35. The method of claim 27, wherein the controller determines values for the plurality of points with data from a therapy session comprising automatic positive airway pressure (APAP) therapy.

36. The method of claim 27, further comprising conditioning the analysis on checking of a time of therapy use and/or a range of provided therapy pressures of a therapy session.

37. The method of claim 27, further comprising estimating a leak flow rate from the measured pressure, the measured flow rate, and the determined parameters.

38. The method of claim 37 further comprising determining a bias flow rate based on a pressure-flow curve defined by the determined parameters.

39. The method of claim 38 wherein determining the leak flow estimate comprises subtracting the bias flow rate from the measured flow rate, wherein the measured flow rate comprises a total flow rate.

40. The method of claim 38, wherein the pressure-flow curve defined by the determined parameters comprises a quadratic function.

41. The method of claim 38, further comprising determining the bias flow rate by inverting the pressure-flow curve defined by the determined parameters.

42. The method of claim 37, further comprising estimating a respiratory flow rate of the patient from the measured flow rate, the measured pressure, the determined parameters, and the estimated leak flow rate.

43. The method of claim 42, further comprising:

detecting an event from the estimated respiratory flow rate of the patient, and adjusting a treatment pressure of the flow of air in response to the detected event.

44. The method of claim 43, wherein the event is an event from the group consisting of: an apnea, a hypopnea, a snore, and inspiratory flow limitation.

45. The method of claim 27, wherein the analysing further comprises:

comparing the determined parameters to a plurality of sets of parameters in a database, and identifying the patient interface based on the determined parameters.

46. The method of claim 27, wherein the template curve is a quadratic function.

47. The method of claim 27, further comprising determining a vent blocking event based on the determined parameters.

48. The method of claim 47 wherein the determining the vent blocking event comprises comparing a measure of average total flow rate with a flow rate at a given device pressure according to a function comprising the determined parameters.

49. The method of claim 48 generating an indication of the vent blocking event if the measure of average total flow rate is less than the flow rate according to the function.

50. A non-transitory processor readable medium configured with program instructions for controlling one or more processors to execute a method of operating a respiratory treatment apparatus, the method comprising the method of claim 27.

51. Respiratory treatment apparatus comprising:

a pressure generator configured to generate a flow of air to a patient interface for a respiratory therapy for a patient;

a pressure transducer configured to generate a signal representing a pressure of the flow of air;

a flow rate transducer configured to generate a signal representing a flow rate of the flow of air; and a controller comprising one or more processors with the non-transitory processor readable medium of claim 50.

52. A system for controlling a respiratory therapy, comprising:

means for supplying a flow of air to a patient interface as a respiratory therapy;

means for generating a flow rate signal representing a flow rate of the flow of air;

means for generating a pressure signal representing a pressure of the flow of air;

means for analysing the flow rate signal and the pressure signal to identify the patient interface; and means for adjusting a property of the flow of air based on the identified patient interface, wherein the analysing comprises determining of parameters that best fit a template curve to a plurality of points, each point comprising: (a) a pressure value, and (b) a flow rate value at the pressure value.

* * * * *